(12) United States Patent
Malle et al.

(10) Patent No.: US 9,604,992 B2
(45) Date of Patent: Mar. 28, 2017

(54) COMPOUNDS OF DIBENZYLIDENE SORBITOL ESTER TYPE, PROCESS OF PREPARATION, USE, COMPOSITIONS COMPRISING THEM AND COSMETIC TREATMENT METHOD

(75) Inventors: Gerard Malle, Villiers S/Morin (FR); Tiina Luukas, Sevran (FR)

(73) Assignee: L'Oreal, Paris (FR)

( * ) Notice: Subject to any disclaimer, the term of this patent is extended or adjusted under 35 U.S.C. 154(b) by 76 days.

(21) Appl. No.: 13/581,915

(22) PCT Filed: Feb. 25, 2011

(86) PCT No.: PCT/EP2011/052821
§ 371 (c)(1),
(2), (4) Date: Oct. 25, 2012

(87) PCT Pub. No.: WO2011/107403
PCT Pub. Date: Sep. 9, 2011

(65) Prior Publication Data
US 2013/0039862 A1 Feb. 14, 2013

Related U.S. Application Data

(60) Provisional application No. 61/310,391, filed on Mar. 4, 2010.

(30) Foreign Application Priority Data

Mar. 2, 2010 (FR) .................... 10 51474

(51) Int. Cl.
*C07D 519/00* (2006.01)
*C07D 493/04* (2006.01)
(Continued)

(52) U.S. Cl.
CPC ......... *C07D 493/04* (2013.01); *C07D 519/00* (2013.01)

(58) Field of Classification Search
CPC ...... C07D 519/00; C07D 493/04; A61K 8/49; A61K 8/58; A61K 8/97; A61K 8/98;
(Continued)

(56) References Cited

U.S. PATENT DOCUMENTS

| 4,743,444 A | 5/1988 | McCall |
| 5,286,755 A | 2/1994 | Kauffmann et al. |

FOREIGN PATENT DOCUMENTS

| EP | 0 918 057 A1 | 5/1999 |
| JP | H05 194114 A | 8/1993 |

OTHER PUBLICATIONS

Feng et al, caplus an 2007:516382.*
(Continued)

*Primary Examiner* — Sun Jae Yoo

(74) *Attorney, Agent, or Firm* — Polsinelli PC

(57) ABSTRACT

The invention relates to novel compounds of dibenzylidene sorbitol ester type corresponding to the following formulae (I) and (II):

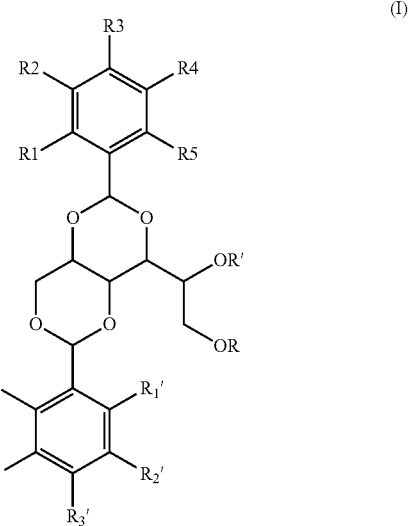

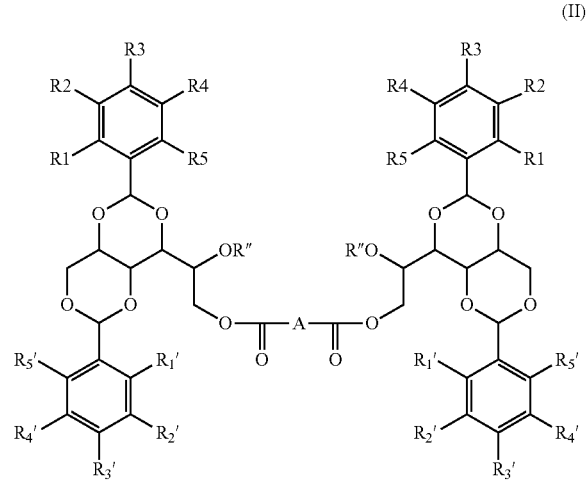

in which:
R, R' and R" represent a hydrogen atom or a —C(O)Y radical in which Y represents a $C_2$-$C_{25}$ hydrocarbon radical or an optionally substituted aryl radical;
the R1, R2, R3, R4, R5, R'1, R'2, R'3, R'4 and R'5 radicals represent a hydrogen atom; a $C_1$-$C_{18}$ alkyl radical; a $C_1$-$C_{18}$ alkoxy radical; a phenoxy radical; an optionally substituted phenyl radical; or a benzyl radical;
the divalent radical A represents, in the formula (II), a $C_1$-$C_{52}$ hydrocarbon radical; an optionally substituted arylene radical; or a silicone radical.

The invention also relates to their process of preparation, to their use in structuring lipophilic media, in particular oils, to (Continued)

the cosmetic or pharmaceutical compositions comprising them and to a cosmetic treatment method employing them.

13 Claims, No Drawings

(51) Int. Cl.
    *A61K 8/49*     (2006.01)
    *A61K 8/58*     (2006.01)
    *A61K 8/97*     (2006.01)
    *A61K 8/98*     (2006.01)
    *A61K 47/22*     (2006.01)
    *A61K 47/24*     (2006.01)
    *A61K 47/46*     (2006.01)
    *A61Q 19/00*     (2006.01)
    *C07F 7/18*     (2006.01)

(58) Field of Classification Search
    CPC ........ A61K 47/22; A61K 47/24; A61K 47/46; A61Q 19/00; C07F 7/18
    See application file for complete search history.

(56) References Cited

OTHER PUBLICATIONS

Brecknell et al., 1977, caplus an 1977:43942.*
Feng et al., "Synthesis of Dibenzylidene Sorbitol Series Compound", Transactions of Tianjin University, vol. 13, No. 1, Feb. 2007, pp. 35-41.
Wolfe et al., "1,2,3,4-Dibenzylidene-D-sorbitol", Journal of the American Chemical Society, vol. 64, No. 7, Jul. 6, 1942, pp. 1493-1497.
Serebryakov et al., "Chiral complexing agents and phase-transfer agents. Communication 2. Synthesis of disubstituted 18-crown-6 ethers with $C_2$ Symmetry starting from D-sorbitol", Bulletin of the Academy of Sciences of the USSR, Division of Chemical Sciences, vol. 37, No. 1, 1988, pp. 101-106.
International Search Report issued Apr. 20, 2011 in PCT/EP2011/052821.

* cited by examiner

COMPOUNDS OF DIBENZYLIDENE SORBITOL ESTER TYPE, PROCESS OF PREPARATION, USE, COMPOSITIONS COMPRISING THEM AND COSMETIC TREATMENT METHOD

CROSS REFERENCE TO RELATED APPLICATIONS

This application is a National Phase filing under 35 U.S.C. §371 of PCT/EP2011/052821 filed on Feb. 25, 2011; and this application claims priority to Application No. 1051474 filed in France on Mar. 2, 2010 under 35 U.S.C. §119, which claims the benefit of U.S. Provisional Application No. 61/310,391 filed on Mar. 4, 2010; the entire contents of all are hereby incorporated by reference.

A subject-matter of the present invention is novel dibenzylidene sorbitol esters, their process of preparation, their use in structuring lipophilic media, in particular oils, the cosmetic compositions comprising them and a cosmetic treatment method employing them.

Cosmetic compositions are generally thickened in order to make possible easy application. The formulator has available a great many possibilities for thickening and gelling both hydrophilic media and lipophilic media, such as oils. Thus, in order to thicken oils until sticks are obtained which simultaneously have a satisfactory consistency, an acceptable stability over time and a suitable disintegrability, a person skilled in the art generally uses crystallizable compounds which are essentially waxes, such as polyethylene waxes, candelilla waxes, carnauba waxes or beeswaxes, and pasty compounds, predominantly lanolins. Generally, a mixture composed of 50-70% of oils and of pasty compounds can be brought to a level of consistency which makes possible the manufacture of a disintegrable stick by addition of 12-20% of waxes. However, the sticks thus obtained have the disadvantages of being matt and easily broken.

An aim of the present invention is in particular to overcome this disadvantage by providing novel compounds capable of being employed to structure or thicken lipophilic media, in particular oils, and thus to result in the production of glossy sticks which are not easily broken.

After much research, the Applicant Company has discovered, surprisingly and unexpectedly, that a novel family of dibenzylidene sorbitol esters can make it possible to achieve this objective and in particular to increase the consistency of the oils until a consistency of stick type is obtained, the said stick furthermore being much softer and much less easily broken than normal sticks based on waxes, which disintegrate very easily, and making it possible to obtain an easy, exact, fast and effortless deposition.

It has been found that it is possible, with the dibenzylidene sorbitol esters according to the invention, to completely or partially replace waxes normally employed.

A subject-matter of the present invention is thus a compound of dibenzylidene sorbitol ester type corresponding to one of the formulae (I) and (II) as defined below.

Another subject-matter of the invention is a process for the preparation of the said compounds of formula (I) or (II).

Another subject-matter of the invention is a cosmetic or pharmaceutical composition comprising, in a physiologically acceptable medium, at least one such compound of formula (I) or (II).

Yet another subject-matter of the invention is the use of at least one such compound of formula (I) or (II) as structuring agent, thickening agent or gelling agent, in particular for a lipophilic medium, especially in a cosmetic or pharmaceutical composition preferably comprising at least one compound chosen from volatile or nonvolatile and carbon-comprising, hydrocarbon-comprising, fluorine-comprising and/or silicone-comprising oils and/or solvents of mineral, animal, vegetable or synthetic origin, alone or as mixtures.

Dibenzylidene sorbitol, also known as dibenzaldehyde monosorbitol acetal or DBS, is a well known compound which makes it possible to suitably structure some polar solvents, such as lower alcohols (ethanol, isopropanol), diols and triols (propylene glycol, 1,3-propanediol, 1,3-butylene glycol, glycerol) or also liquid polyglycols (polyethylene glycol, polypropylene glycol). Mention may in particular be made of U.S. Pat. No. 4,154,816, U.S. Pat. No. 4,743,444 or U.S. Pat. No. 4,816,261, which provide for the use thereof in obtaining antiperspirant sticks based on alcohols, diols and/or polyols.

Provision has also been made, in U.S. Pat. No. 5,609,855, for the use of substituted derivatives of DBS which are more stable in an acidic medium, dibenzylidene alditols, in order to obtain antiperspirant sticks having very good stability.

Mention may also be made of EP 0 531 224, which describes sticks based on polyols and water which are obtained by combining substituted derivatives of DBS, of dibenzylidene-ose type, and a hardening agent of sulphosuccinate type.

Provision has been made, in JP05025077, to use $C_{10}$-$C_{22}$ sorbitol ethers to emulsify oils and to thicken them.

However, dibenzylidene sorbitol and the derivatives mentioned above do not make it possible to sufficiently thicken oils so as to be able to manufacture sticks of appropriate consistency which are capable of suitably disintegrating.

The dibenzylidene sorbitol esters according to the invention for their part make it possible to obtain lipstick sticks which are both translucent and glossy, in contrast to conventional sticks based on waxes and pasty compounds which constitute the state of the art and which result in matt and opaque sticks; the sticks according to the invention in addition exhibit both good stability and excellent disintegrability, making it possible to carry out easy and exact depositions.

It has also been found that the sticks obtained with the dibenzylidene sorbitol esters according to the invention are advantageously much more transparent than normal sticks based on waxes.

Furthermore, the cosmetic compositions according to the invention exhibit good applicability and good coverage; good adhesion to the support, whether on the nail, hair, eyelashes, skin or lips; an appropriate flexibility and an appropriate strength of the film, in order to prevent cracks, for example in the case of lipsticks; and an excellent level of lasting glossiness. The comfort and slip properties are also highly satisfactory.

In the present description, the term "aryl" is understood to mean any substituent deriving from an aromatic ring system, such as, in particular, benzyl, phenyl, tolyl, xylyl or naphthyl, and their forms substituted by one or more alkyls, such as phenethyl (phenylethyl) or methylnaphthyl, for example.

The dibenzylidene sorbitol esters capable of being used in the context of the present invention correspond to the following formulae (I) and (II):

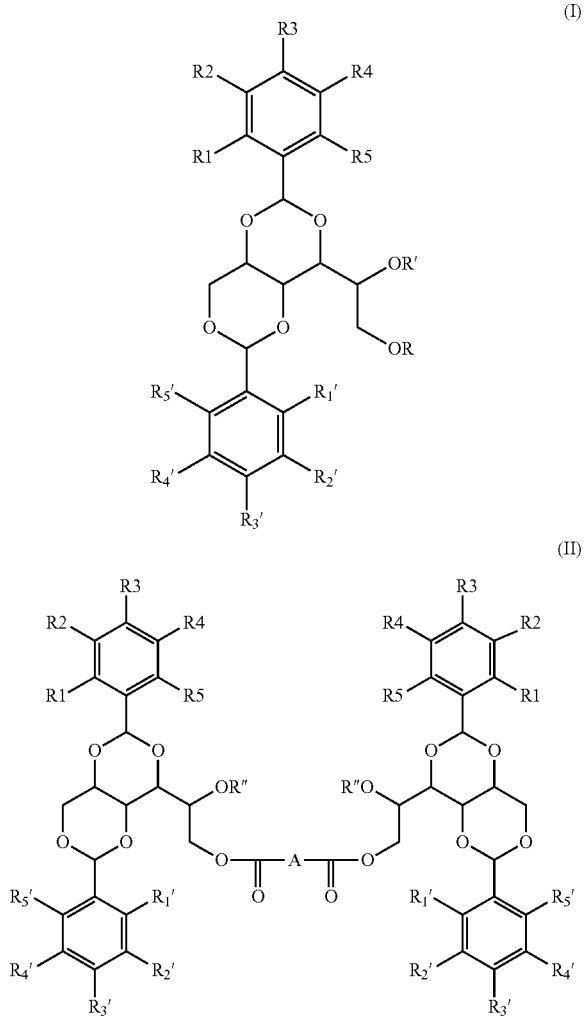

In these formulae, R, R' and R" represent, independently of one another, a hydrogen atom or a —C(O)Y radical in which Y represents:
  either a saturated or unsaturated and linear, branched and/or cyclic $C_2$-$C_{25}$, preferably $C_3$-$C_{23}$ and better still $C_4$-$C_{21}$ hydrocarbon radical;
  or an aryl radical comprising from 5 to 14 carbon atoms which is optionally substituted by from 1 to 3 saturated or unsaturated and linear, branched and/or cyclic $C_1$-$C_{32}$, in particular $C_2$-$C_{12}$, indeed even $C_3$-$C_8$, hydrocarbon radicals; it being understood that R and R' cannot simultaneously represent a hydrogen atom.

When Y is a hydrocarbon radical, it is preferably a $C_2$-$C_{25}$, preferably $C_3$-$C_{23}$, better still $C_4$-$C_{21}$, indeed even $C_6$-$C_{19}$, (saturated and linear or branched) alkyl radical; or else a $C_5$-$C_6$ cyclic (cycloalkyl) radical which is optionally substituted by from 1 to 3 methyls or by a linear or branched $C_2$-$C_8$ alkyl radical; or also a $C_{10}$-$C_{17}$ alkenyl radical comprising one or two conjugated or nonconjugated double bonds.

When Y is an aryl radical, it is preferably chosen from the phenyl radical or a phenyl radical substituted by from 1 to 3 saturated and linear, branched and/or cyclic $C_1$-$C_{32}$, in particular $C_2$-$C_{12}$, indeed even $C_3$-$C_8$, hydrocarbon radicals chosen in particular from methyl, ethyl, propyl, isopropyl, butyl, isobutyl, tert-butyl, pentyl, isopentyl, neopentyl, cyclopentyl, hexyl, cyclohexyl, heptyl, isoheptyl, octyl or isooctyl.

Mention may in particular be made, for Y, of the ethyl, propyl, isopropyl, butyl, isobutyl, tert-butyl, pentyl, isopentyl, neopentyl, 2-ethylpropyl, hexyl, heptyl, isoheptyl, 4-ethylpentyl, 2-ethylhexyl, 4,5-dimethylhexyl, 2-heptylheptyl, 3,5,5-trimethylhexyl, octyl, isooctyl, nonyl, isononyl, decyl, neodecyl, undecyl, lauryl, tridecyl, myristyl, pentadecyl, palmityl, stearyl, isostearyl, arachidyl, behenyl, hexacosanoyl, cyclopentyl, cyclopentylmethyl, 3-cyclopentylpropionyl, cyclohexyl, dimethylcyclohexyl, trimethylcyclohexyl, tert-butylcyclohexyl, n-butylcyclohexyl, cyclohexylmethyl, 4-cyclohexylbutyryl, caproleyl, undecylenyl, dodecylenyl, myristoleyl, palmitoleyl, oleyl, cetoleyl, linoleyl, linolenyl, toluoyl, xylyl, naphthyl, phenyl, 4-(tert-butyl)phenyl, 1-methyl-2-naphthyl, 2-isopropyl-1-naphthyl, benzyl or phenethyl (phenylethyl) radicals.

Preferably, Y is a linear or branched $C_2$-$C_{25}$, preferably $C_3$-$C_{23}$, better still $C_4$-$C_{21}$, indeed even $C_6$-$C_{19}$, alkyl radical.

In the compounds according to the invention of formula (I), it is understood that R and R' cannot simultaneously represent a hydrogen atom. In a preferred embodiment, R'=H and R=COY.

In the compounds according to the invention of formula (II), in a preferred embodiment, R"=H.

In the formulae (I) and (II), the R1, R2, R3, R4, R5, R'1, R'2, R'3, R'4 and R'5 radicals represent, independently of one another:
  a hydrogen atom;
  a linear or branched $C_1$-$C_{18}$ alkyl radical;
  a linear or branched $C_1$-$C_{18}$ alkoxy radical;
  a phenoxy radical;
  a phenyl radical optionally substituted by from 1 to 3 radicals chosen from methyl, ethyl, propyl, isopropyl, butyl, isobutyl or tert-butyl;
  a benzyl radical.

It is also possible for two consecutive radicals, taken together, to form a cyclohexyl ring, the other radicals having the meanings given above.

Thus, the (R1, R2) or (R2, R3) or (R3, R4) or (R4, R5) radicals, taken together, can form a cyclohexyl ring.

Likewise, the (R'1, R'2) or (R'2, R'3) or (R'3, R'4) or (R'4, R'5) radicals, taken together, can form a cyclohexyl ring.

In the compounds of formula (I), preferably at least two of the R1, R2, R3, R4 and R5 radicals represent a hydrogen atom.

In the compounds of formula (I), in a preferred embodiment, all the R1, R2, R3, R4 and R5 radicals and/or all the R'1, R'2, R'3, R'4 and R'5 radicals represent a hydrogen atom.

In the compounds of formula (I), in another preferred embodiment, at least two, preferably two, of the R1, R2, R3, R4 and R5 radicals and/or at least two, preferably two, of the R'1, R'2, R'3, R'4 and R'5 radicals represent a linear or branched C1-C18 alkyl radical, preferably methyl.

Preferably, in the formula (I), when R and R' simultaneously represent a benzoyl radical, at least one of the R1, R2, R3, R4, R5, R'1, R'2, R'3, R'4 and R'5 radicals is other than a hydrogen atom.

In the compounds of formula (II), preferably at least two of the R1, R2, R3, R4 and R5 radicals and at least two of the R'1, R'2, R'3, R'4 and R'5 radicals represent a hydrogen atom.

In the above formula (II), the divalent radical A represents:
- either a saturated or unsaturated and linear, cyclic or branched divalent $C_1$-$C_{52}$, preferably $C_2$-$C_{36}$, better still $C_3$-$C_{36}$, indeed even $C_4$-$C_{34}$, hydrocarbon radical; in particular a $C_1$-$C_{52}$, preferably $C_2$-$C_{34}$, alkylene radical (saturated and linear or branched); and especially a saturated linear $C_8$ or $C_{34}$ alkylene radical;
- or a $C_6$-$C_{14}$, better still $C_8$-$C_{12}$, divalent arylene radical optionally substituted by from 1 to 3 saturated or unsaturated and linear, branched and/or cyclic $C_1$-$C_{32}$, better still $C_2$-$C_{12}$, indeed even $C_3$-$C_8$, hydrocarbon radicals, in particular alkyl radicals; especially chosen from methyl, ethyl, propyl, isopropyl, butyl, isobutyl, tert-butyl, pentyl, isopentyl, neopentyl, cyclopentyl, hexyl, cyclohexyl, heptyl, isoheptyl, octyl or isooctyl;

Mention may in particular be made of the phenylene (benzenediyl), naphthylene (naphthalenediyl), xylylene or biphenylene radicals.

or a divalent silicone radical of formula (III):

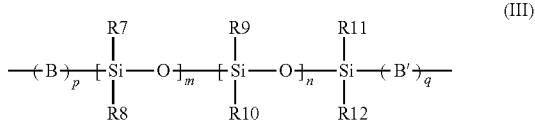

(III)

in which:
- p and q are, independently of one another, 0 or 1,
- B and B' represent, independently of one another, a saturated or unsaturated, indeed even aromatic, and linear, branched and/or cyclic divalent carbon-comprising, in particular hydrocarbon, radical; in particular an alkylene radical; comprising from 1 to 12 carbon atoms, in particular from 2 to 8 carbon atoms, optionally comprising 1 or more heteroatoms chosen from O, S and N, in particular O (especially ether); or else B and B' independently represent a radical of formula —[(CH$_2$)$_x$O]$_z$— with x=1, 2 or 3 and z=1-10;
- R7 to R12 are, independently of one another, a saturated or unsaturated, indeed even aromatic, and linear, branched and/or cyclic carbon-comprising, in particular hydrocarbon, radical comprising from 1 to 20 carbon atoms;
- m and n are, independently of one another, integers between 0 and 140, in particular 1 and 120, and are such that the weight-average molecular weight (Mw) of the radical of formula (III) is between 300 and 20 000.

In particular, B and B' can, independently of one another, represent a divalent radical of formula —(CH$_2$)$_a$— with a=1 to 12, in particular methylene, ethylene or propylene, or a phenylene radical, or else a radical of formula —[(CH$_2$)$_x$O]$_z$— with x=1, 2 or 3 and z=1-10; in particular x=2 or 3 and z=1-4; better still x=3 and z=1.

In particular, R7 to R12 are, independently of one another, a linear or branched alkyl radical comprising from 1 to 20 carbon atoms, in particular from 2 to 12 carbon atoms, or else an aryl radical comprising from 5 to 20 carbon atoms, in particular from 6 to 12 carbon atoms, or also a cycloalkyl radical comprising from 5 to 20 carbon atoms, in particular from 5 to 12 carbon atoms.

Preferably, they are chosen from the methyl, ethyl, propyl, isopropyl, butyl, pentyl, hexyl, octyl, decyl, dodecyl and octadecyl; cyclohexyl; phenyl, naphthyl, benzyl, phenylethyl, tolyl or xylyl radicals.

Preferably, m and n are such that the weight-average molecular weight (Mw) of the radical of formula (III) is between 400 and 10 000, indeed even between 800 and 4000.

The divalent radical A is chosen in particular from the methylene, ethanediyl, propanediyl, butanediyl, pentanediyl, hexanediyl, heptanediyl, octanediyl, nonanediyl, decanediyl, undecanediyl, dodecanediyl, tridecanediyl, tetradecanediyl, pentadecanediyl, hexadecanediyl, heptadecanediyl, octadecanediyl, cyclohexanediyl, benzenediyl, naphthalenediyl, biphenylene or xylylidene radicals; and from radicals resulting from fatty acid dimers (in particular $C_{36}$ dimers), such as the products sold under the names Pripol 1006, 1009, 1013 and 1017 by Uniqema.

The divalent radical A can also be chosen from radicals such as polyalkylsiloxanes, in particular polydimethylsiloxanes; or else polyarylsiloxanes, in particular polyphenylsiloxanes; or also polyaryl/alkylsiloxanes, in particular polyphenyl/methylsiloxane or polyphenyl/propylsiloxane.

Very particularly, A can represent a divalent polydimethylsiloxane radical, in particular having a weight-average molecular weight (Mw) of between 400 and 10 000, indeed even between 500 and 5000, in particular between 800 and 4000.

Mention may be made, as particularly preferred compound of formula (I) or (II), of the following compounds:

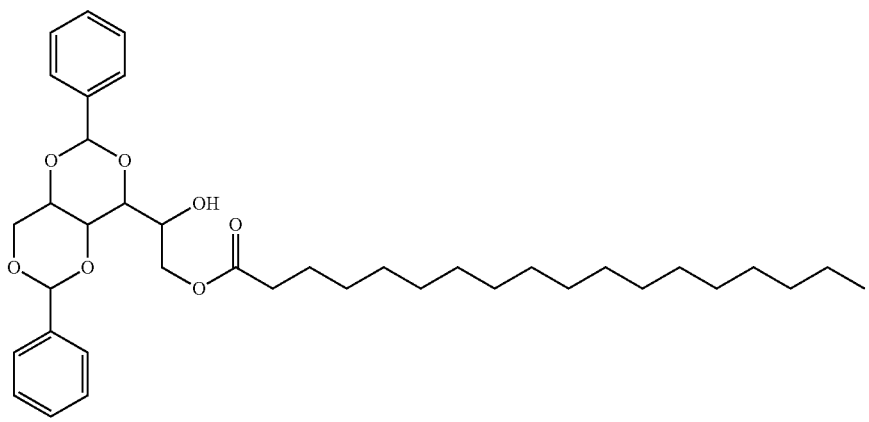 [SMILES: CCCCCCCCCCCCCCCCCC(=O)OCC(O)C1OC(c2ccccc2)OC2COC(c3ccccc3)OC21]

-continued
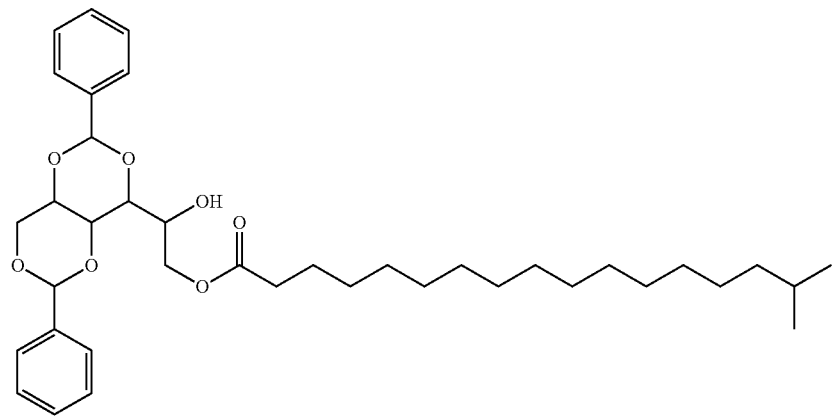 [SMILES: CC(C)CCCCCCCCCCCCCCC(=O)OCC(O)C1OC(c2ccccc2)OC2COC(c3ccccc3)OC21]
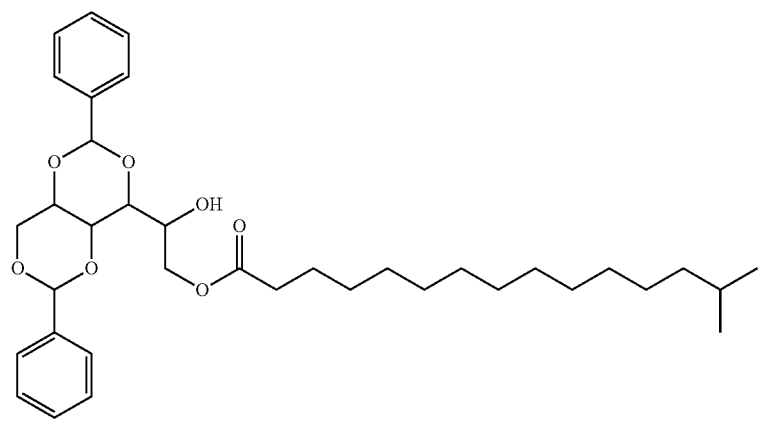 [SMILES: CC(C)CCCCCCCCCCCCC(=O)OCC(O)C1OC(c2ccccc2)OC2COC(c3ccccc3)OC21]
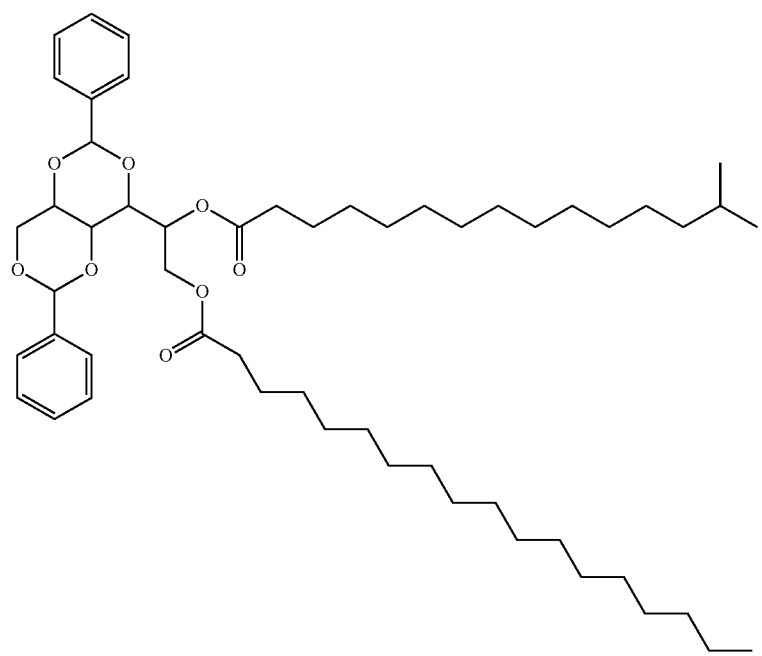 [SMILES: CCCCCCCCCCCCCCCCCC(=O)OCC(OC(=O)CCCCCCCCCCCCC(C)C)C1OC(c2ccccc2)OC2COC(c3ccccc3)OC21]

-continued
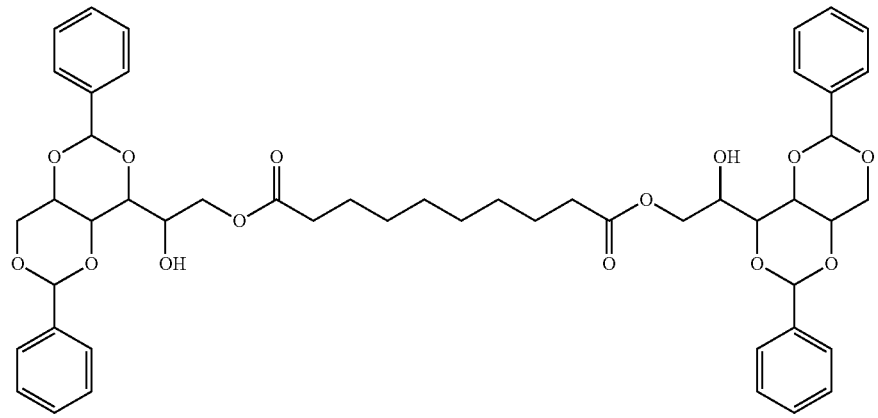 [SMILES: O=C(CCCCCCCCC(=O)OCC(O)C1OC(c2ccccc2)OC2COC(c3ccccc3)OC21)OCC(O)C1OC(c2ccccc2)OC2COC(c3ccccc3)OC21]
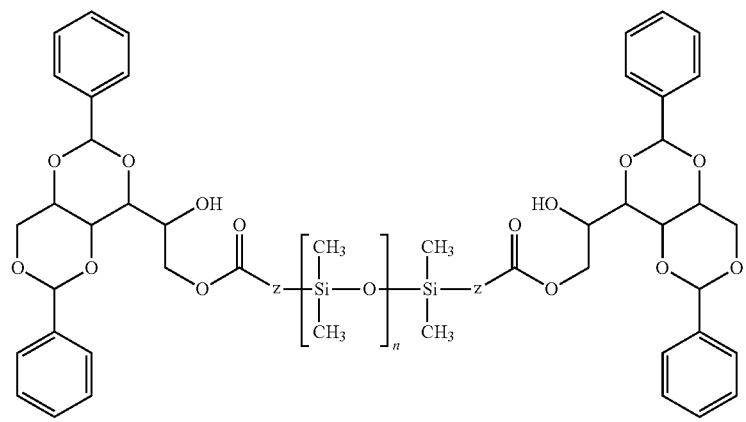
with Z = (CH$_2$)$_3$
and n = 34
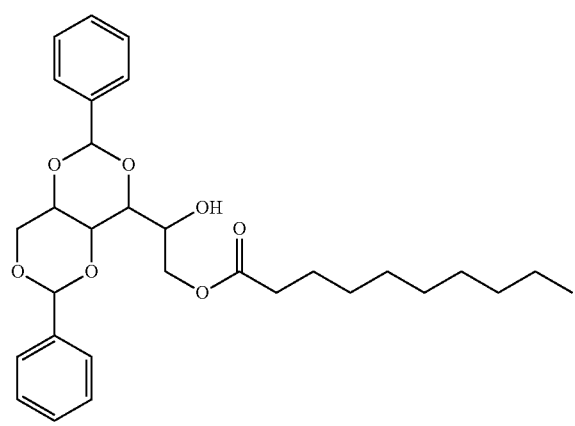 [SMILES: CCCCCCCCCC(=O)OCC(O)C1OC(c2ccccc2)OC2COC(c3ccccc3)OC21]

-continued
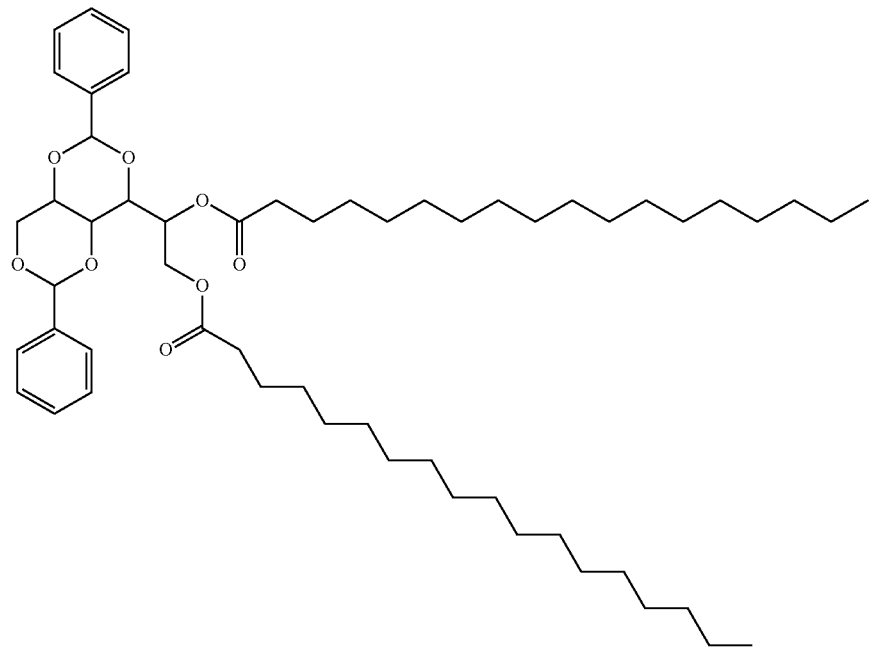 [SMILES: CCCCCCCCCCCCCCCCCC(=O)OCC(OC(=O)CCCCCCCCCCCCCCCCC)C1OC(c2ccccc2)OC2COC(c3ccccc3)OC21]
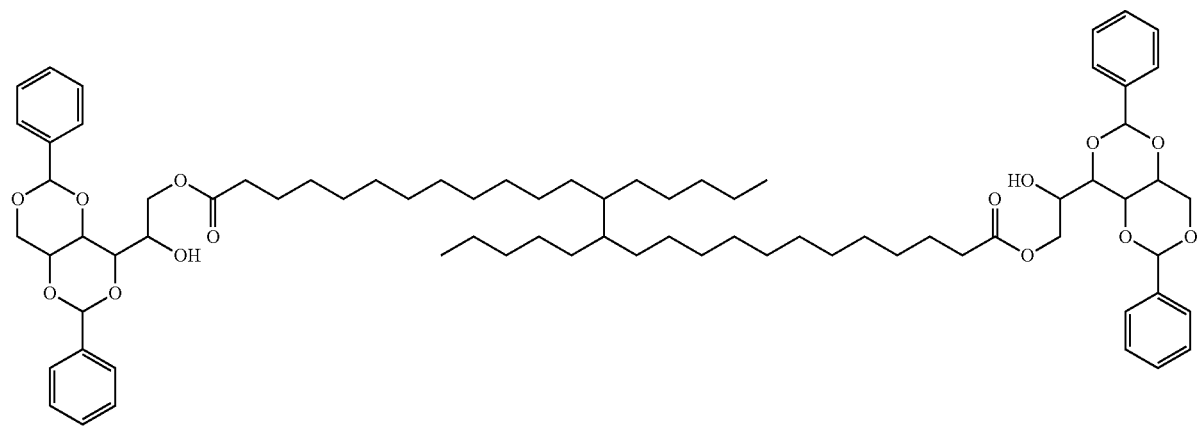 [SMILES: CCCCCC(CCCCCCCCCCCC(=O)OCC(O)C1OC(c2ccccc2)OC2COC(c3ccccc3)OC21)C(CCCCC)CCCCCCCCCCCC(=O)OCC(O)C1OC(c2ccccc2)OC2COC(c3ccccc3)OC21]
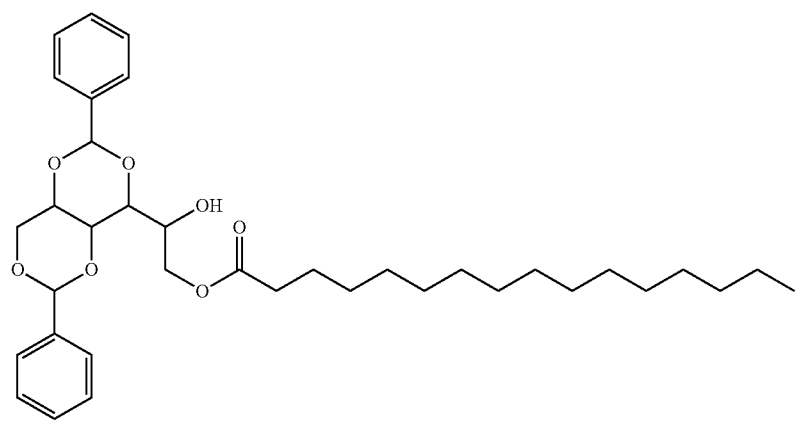 [SMILES: CCCCCCCCCCCCCCCC(=O)OCC(O)C1OC(c2ccccc2)OC2COC(c3ccccc3)OC21]

-continued
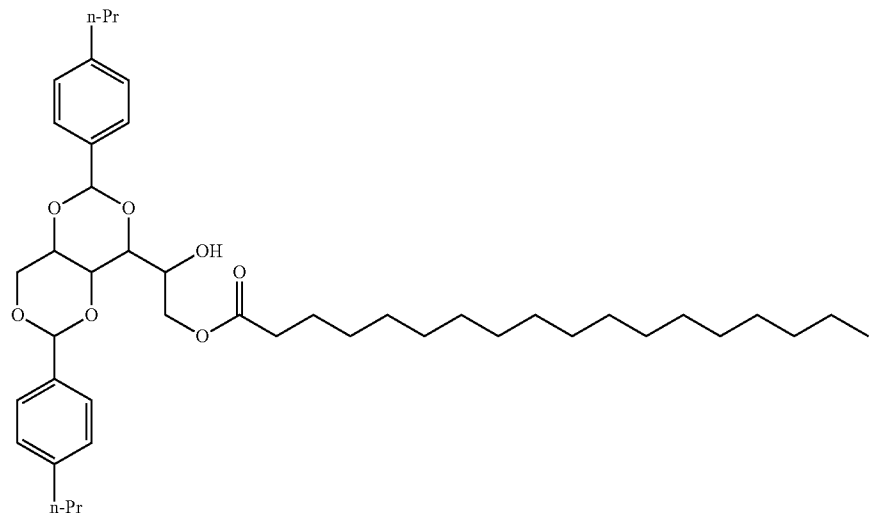
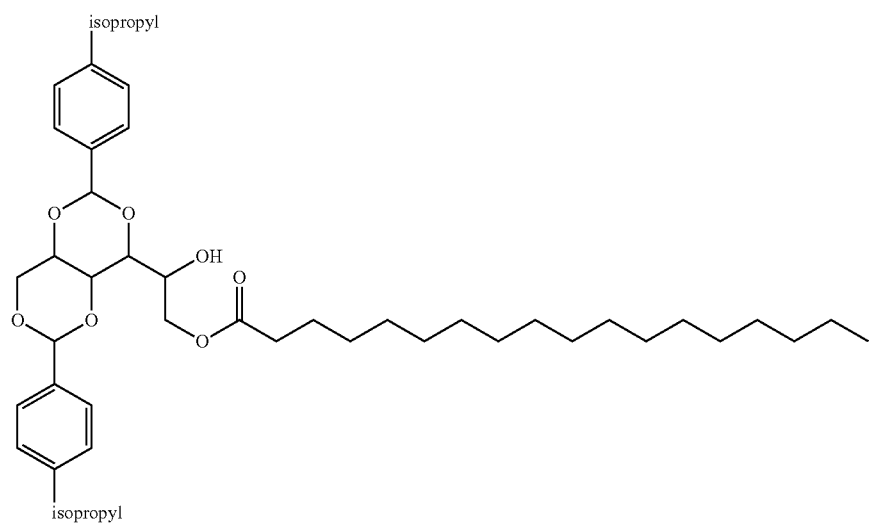
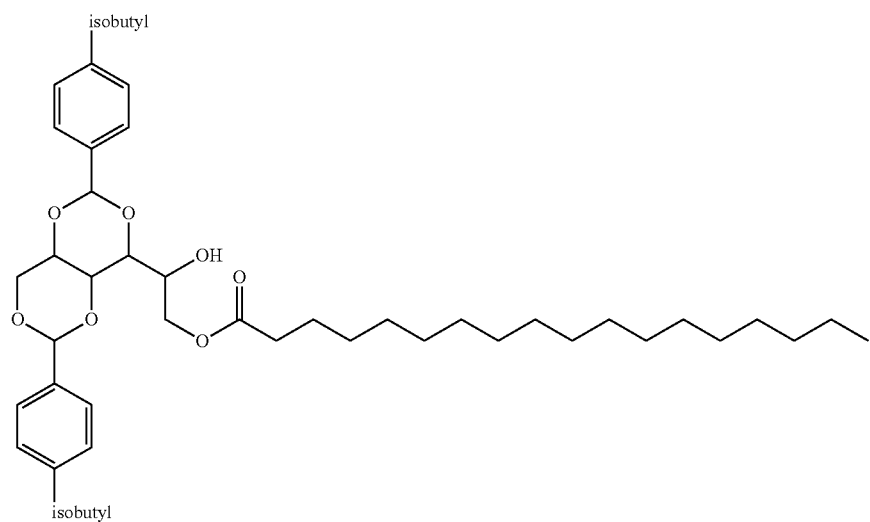

-continued
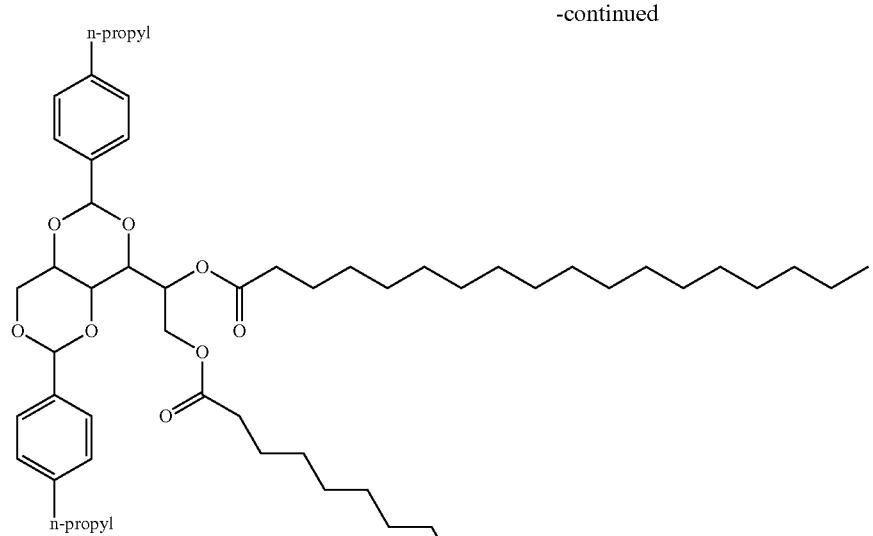
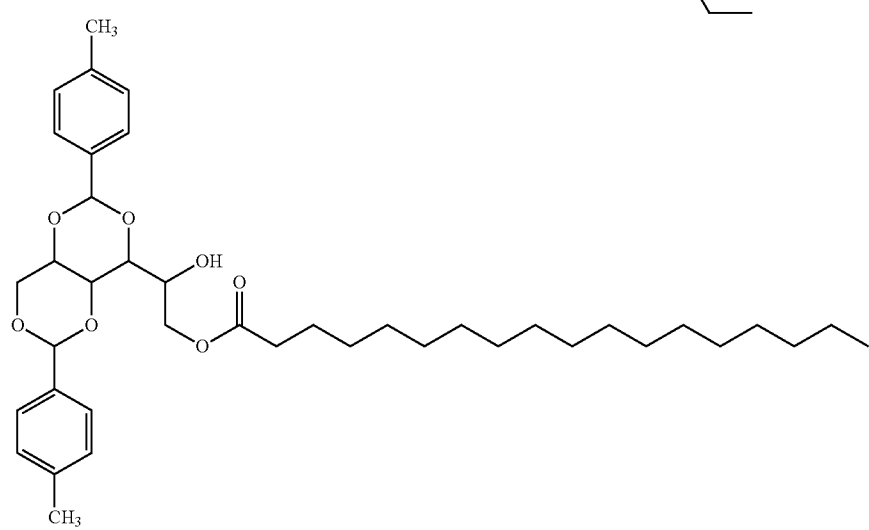
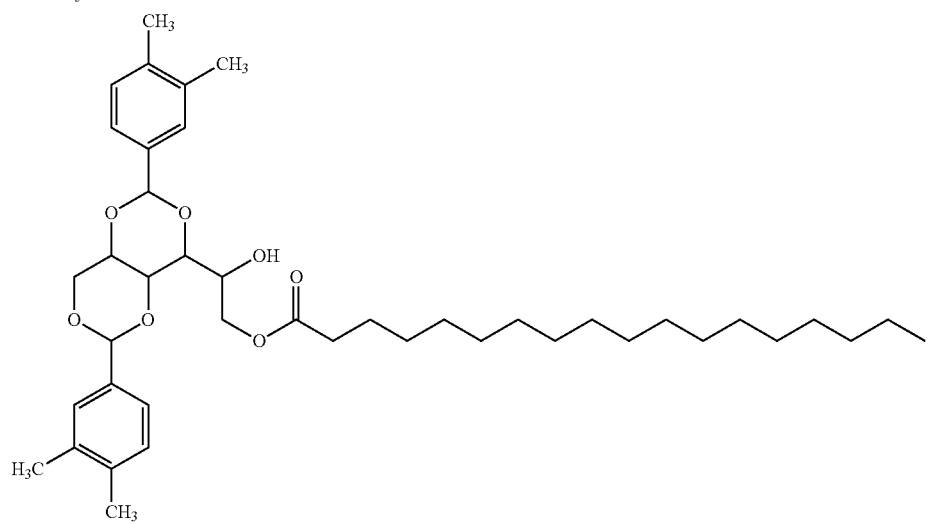

-continued
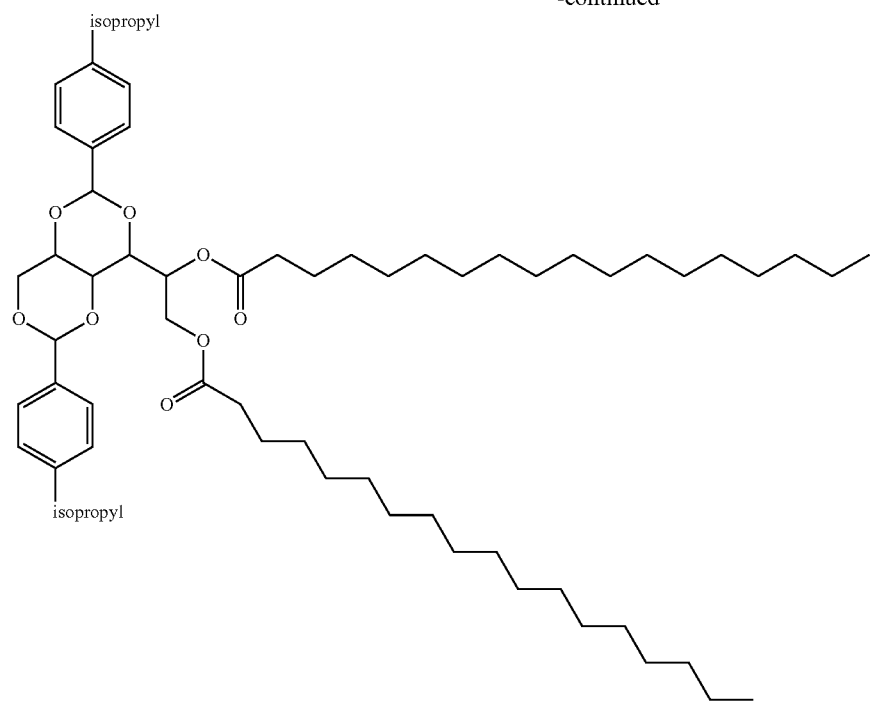
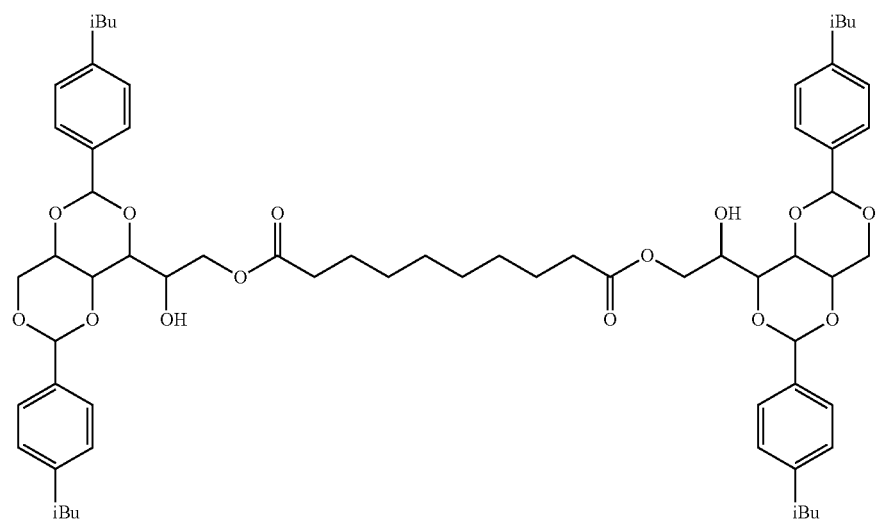
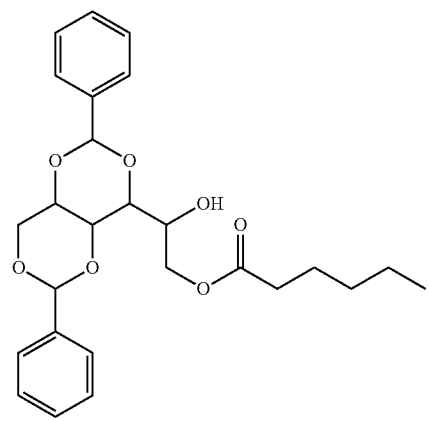

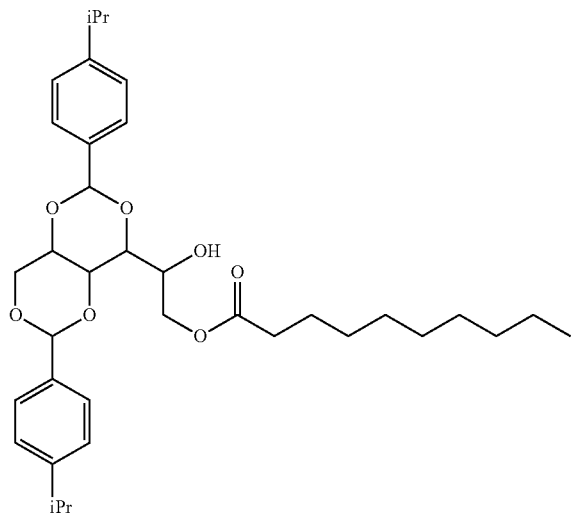

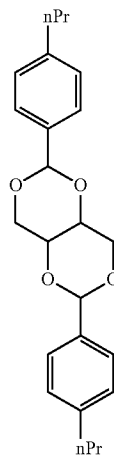

Use may very obviously be made of a mixture of compounds of formula (I) and/or of formula (II).

Another subject-matter of the present invention is a process for the preparation of the compounds of formulae (I) and (II).

The esters according to the invention can be prepared by esterification and transesterification processes normally employed by a person skilled in the art.

A general process for the preparation of the compounds of formula (I) can comprise a stage in which a dibenzylidene sorbitol derivative of formula (A) below is reacted with at least one acid halide of formula Y—C(O)—Hal, preferably an acid chloride, in an aprotic solvent, such as, for example, acetonitrile, toluene, xylene, ethyl acetate, isopropyl acetate, tetrahydrofuran or methyltetrahydrofuran, in the presence of a base, which can be organic or inorganic, such as, for example, a tertiary amine, at a temperature which can be between 40° C. and the boiling point of the solvent chosen.

When, in the compound of formula (I), Y is different from Y', use is made of a mixture of acid halides, which halides can then be added simultaneously and/or sequentially.

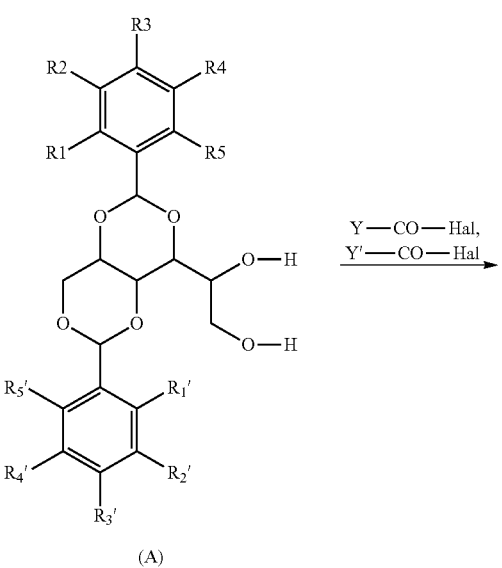

(A)

-continued

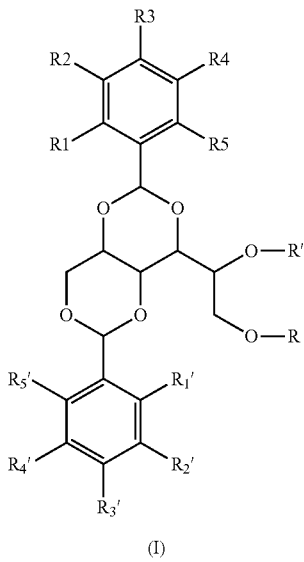

(I)

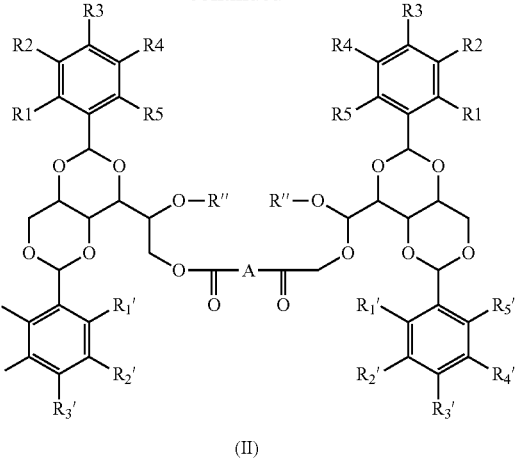

(II)

A general process for the preparation of the compounds of formula (II) can comprise a stage in which a dibenzylidene sorbitol derivative of formula (A) is reacted with an acid dihalide Hal-CO-A-CO-Hal, preferably an acid dichloride, and optionally an acid halide Y—C(O)—Hal, preferably an acid chloride, in an aprotic solvent, such as acetonitrile, toluene, xylene, ethyl acetate, isopropyl acetate, tetrahydrofuran or methyltetrahydrofuran, in the presence of a base, which can be organic or inorganic, such as, for example, a tertiary amine, at a temperature which can be between 40° C. and the boiling point of the solvent chosen.

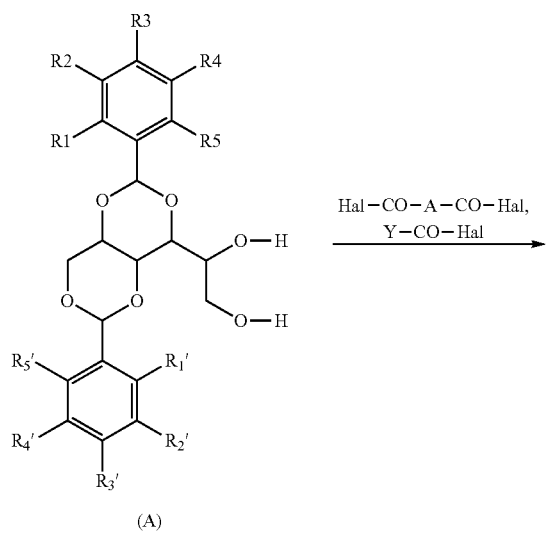

(A)

The dibenzylidene sorbitol esters of formula (I) or (II) according to the invention can advantageously be used in a composition, in particular a cosmetic or pharmaceutical composition, which furthermore comprises a physiologically acceptable medium, in particular a cosmetically or pharmaceutically acceptable medium, that is to say a medium compatible with keratinous substances, such as the skin of the face or of the body, the lips, the hair, the eyelashes, the eyebrows and the nails.

This is because it has been found that the dibenzylidene sorbitol esters according to the invention can make it possible to structure the cosmetic oily media normally employed and in particular vegetable oils, $C_6$-$C_{32}$ alkanes, $C_8$-$C_{32}$ fatty esters, $C_8$-$C_{32}$ fatty alcohols, $C_3$-$C_8$ esters or silicone oils and more particularly the media comprising at least isododecane, decane, undecane, dodecane, tridecane, tetradecane, Parleam, isononyl isononanoate, octyldodecanol, phenyl trimethicone, $C_{12}$-$C_{15}$ alkyl benzoate, ethyl acetate, butyl acetate and their mixtures.

The compounds according to the invention can also have application in the field of the paint, varnish and adhesive industries, as structuring or thickening agent, indeed even gelling agent.

The amount of the said esters according to the invention present in the compositions depends, of course, on the type of composition, which can range from a fluid gel to a stick, and/or on the properties desired; it can be between 0.05 and 30% by weight, preferably between 0.1 and 25% by weight, in particular between 0.2 and 20% by weight, indeed even between 0.5 and 18% by weight and better still between 1 and 16% by weight, with respect to the total weight of the final cosmetic or pharmaceutical composition.

The composition according to the invention furthermore comprises a physiologically acceptable medium, in particular a cosmetically acceptable medium, which can comprise, according to the application envisaged, the constituents normal to this type of composition.

The composition according to the invention can thus advantageously comprise a fatty phase, in particular a liquid fatty phase, which can comprise at least one compound chosen from volatile or nonvolatile and carbon-comprising, hydrocarbon-comprising, fluorine-comprising and/or silicone-comprising oils and/or solvents of mineral, animal, vegetable or synthetic origin, alone or as mixtures insofar as they form a homogeneous and stable mixture and are compatible with the use envisaged.

The term "volatile" is understood to mean, within the meaning of the invention, any compound capable of evaporating on contact with keratinous substances or the lips in less than one hour, at ambient temperature (25° C.) and atmospheric pressure (1 atm). In particular, this volatile compound has a nonzero vapour pressure, at ambient temperature and atmospheric pressure, in particular ranging from 0.13 Pa to 40 000 Pa ($10^{-3}$ to 300 mmHg), especially ranging from 1.3 Pa to 13 000 Pa (0.01 to 100 mmHg). In contrast, the term "nonvolatile" is understood to mean a compound which remains on keratinous substances or the lips, at ambient temperature and atmospheric pressure, for at least one hour and which has in particular a vapour pressure of less than $10^{-3}$ mmHg (0.13 Pa).

Preferably, the physiologically acceptable medium of the composition according to the invention can comprise at least one oil and/or one solvent chosen from, alone or as mixtures:

1/ esters of monocarboxylic acids with monoalcohols and polyalcohols; advantageously, the said ester is a $C_{12}$-$C_{15}$ alkylbenzoate or corresponds to the following formula: $R'_1$—COO—$R'_2$, where:

$R'_1$ represents a linear or branched alkyl radical of 1 to 40 carbon atoms, preferably of 7 to 19 carbon atoms, optionally comprising one or more ethylenic double bonds and optionally substituted, the hydrocarbon chain of which can be interrupted by one or more heteroatoms chosen from N and O and/or one or more carbonyl functional groups, and $R'_2$ represents a linear or branched alkyl radical of 1 to 40 carbon atoms, preferably of 2 to 30 carbon atoms and better still of 3 to 20 carbon atoms, optionally comprising one or more ethylenic double bonds and optionally substituted, the hydrocarbon chain of which can be interrupted by one or more heteroatoms chosen from N and O and/or one or more carbonyl functional groups. The term "optionally substituted" is understood to mean that $R'_1$ and/or $R'_2$ can carry one or more substituents chosen, for example, from groups comprising one or more heteroatoms chosen from O and/or N, such as amino, amine, alkoxy or hydroxyl. Examples of the $R'_1$ groups are those derived from the acids chosen from the group consisting of acetic, propionic, butyric, caproic, caprylic, pelargonic, capric, undecanoic, lauric, myristic, palmitic, stearic, isostearic, arachidic, behenic, oleic, linolenic, linoleic, oleostearic, arachidonic and erucic acid and of their mixtures. Preferably, $R'_1$ is an unsubstituted branched alkyl group having from 1 to 14 carbon atoms, preferably from 4 to 10 carbon atoms, and $R'_2$ is an unsubstituted branched alkyl group having from 2 to 15 carbon atoms, preferably from 5 to 11 carbon atoms.

Mention may in particular be made of $C_4$-$C_{48}$ esters, optionally incorporating, in their hydrocarbon chain, one or more heteroatoms chosen from N and O and/or one or more carbonyl functional groups, and more particularly ethyl, propyl, isopropyl, butyl, amyl or isoamyl acetate; Purcellin oil (cetearyl octanoate), isononyl isononanoate, isopropyl myristate, isopropyl palmitate, 2-ethylhexyl palmitate, 2-octyldodecyl stearate, 2-octyldodecyl erucate, isostearyl isostearate, $C_{12}$ to $C_{15}$ alkyl benzoate, hexyl laurate or diisopropyl adipate; hexanoates, heptanoates, octanoates, decanoates or ricinoleates of alcohols or polyalcohols, for example of fatty alcohols, such as propylene glycol dioctanoate, and also isopropyl N-lauroyl sarcosinate (in particular Eldew-205SL from Ajinomoto); hydroxylated esters, such as ethyl lactate, isostearyl lactate or diisostearyl malate; and pentaerythritol esters; branched $C_8$-$C_{16}$ esters, in particular isohexyl neopentanoate.

2/ hydrocarbon vegetable oils with a high content of triglycerides composed of esters of fatty acids and of glycerol, the fatty acids of which can have various chain lengths from $C_4$ to $C_{24}$, it being possible for the chains to be linear or branched and saturated or unsaturated; these oils are in particular wheat germ, maize, sunflower, shea, castor, sweet almond, macadamia, apricot, soybean, rapeseed, cottonseed, alfalfa, poppy, pumpkinseed, sesame, cucumber, avocado, hazelnut, grape seed, blackcurrant seed, evening primrose, millet, barley, quinoa, olive, rye, safflower, candlenut, passionflower, musk rose, jojoba, palm or calophyllum oil; or triglycerides of caprylic/capric acids, such as those sold by Stéarinerie Dubois or those sold under the names "Miglyol 810®", "812®" and "818®" by Dynamit Nobel.

3/ $C_6$-$C_{32}$, in particular $C_{12}$-$C_{26}$ alcohols and in particular monoalcohols, such as oleyl alcohol, linoleyl alcohol, linolenyl alcohol, isostearyl alcohol, 2-hexyldecanol, 2-butyloctanol, 2-undecylpentadecanol and octyldodecanol;

4/ volatile or nonvolatile and linear or branched hydrocarbon oils of synthetic or mineral origin which can be chosen from hydrocarbon oils having from 5 to 100 carbon atoms, in particular petrolatum, polydecenes, hydrogenated polyisobutenes, such as Parleam, squalane, perhydrosqualene and their mixtures. Mention may more particularly be made of linear, branched and/or cyclic $C_5$-$C_{48}$ alkanes and preferably branched $C_8$-$C_{16}$ alkanes, such as $C_8$-$C_{16}$ isoalkanes of petroleum origin (also known as isoparaffins); in particular decane, heptane, undecane, dodecane, tridecane, tetradecane or cyclohexane; and also isododecane, isodecane or isohexadecane; and their mixtures.

5/ volatile or nonvolatile silicone oils;

Mention may be made, as volatile silicone oils, of volatile linear or cyclic silicone oils, in particular those having a viscosity of less than 8 centistokes and having in particular from 2 to 10 silicon atoms, these silicones optionally comprising alkyl or alkoxy groups having from 1 to 22 carbon atoms, in particular octamethylcyclotetrasiloxane, decamethylcyclopentasiloxane, dodecamethyl-cyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, methylhexyldimethylsiloxane and their mixtures.

The nonvolatile silicone oils which can be used according to the invention can be polydimethylsiloxanes (PDMSs), polydimethylsiloxanes comprising pendant alkyl or alkoxy groups and/or alkyl or alkoxy groups at the end of the silicone chain, which groups each have from 2 to 24 carbon atoms, or phenylated silicones, such as phenyl trimethicones, phenyl dimethicones, phenyltrimethylsiloxydiphenyl-siloxanes, diphenyl dimethicones, diphenylmethyldiphenyltrisiloxanes or (2-phenylethyl) trimethylsiloxysilicates.

In addition, the fatty phase can comprise additional oils and/or solvents which can be chosen, alone or as mixtures, from:

fluorinated oils, such as perfluoropolyethers, perfluoroalkanes, such as perfluorodecalin, perfluoroadamantanes, monoesters, diesters and triesters of perfluoroalkyl phosphates and fluorinated ester oils;

oils of animal origin;

$C_6$-$C_{40}$ ethers, in particular $C_{10}$-$C_{30}$ ethers, such as propylene glycol ethers which are liquid at ambient temperature, such as propylene glycol monomethyl ether, propylene glycol monomethyl ether acetate, or dipropylene glycol mono(n-butyl)ether;

$C_8$-$C_{32}$ fatty acids, such as oleic acid, linoleic acid, linolenic acid and their mixtures;

bifunctional oils comprising two functional groups chosen from ester and/or amide and comprising from 6 to 30 carbon atoms, in particular from 8 to 28 carbon atoms, and 4 heteroatoms chosen from O and N, the amide and ester functional groups preferably being in the chain;

ketones which are liquid at ambient temperature (25° C.), such as methyl ethyl ketone, methyl isobutyl ketone, diisobutyl ketone, isophorone, cyclohexanone or acetone;

aldehydes which are liquid at ambient temperature, such as benzaldehyde or acetaldehyde.

The liquid fatty phase can represent from 1 to 99% by weight of the composition, in particular from 2 to 90% by weight, especially from 5 to 75% by weight, indeed even from 10 to 60% by weight, better still from 20 to 55% by weight, of the total weight of the composition.

The composition can also comprise fatty substances which are solid at ambient temperature, such as waxes, pasty fatty substances, gums and their mixtures. They can be of animal, vegetable, mineral or synthetic origin.

The term "wax" is understood to mean, within the meaning of the present invention, a lipophilic compound which is solid at ambient temperature (25° C.), which exhibits a reversible solid/liquid change in state and which has a melting point of greater than or equal to 25° C. which can range up to 120° C. On bringing the wax to the liquid state (melting), it is possible to render it miscible with the oils which may be present and to form a microscopically homogeneous mixture but, on bringing the temperature of the mixture back to ambient temperature, recrystallization of the wax in the oils of the mixture is obtained. The melting point of the wax can be measured using a differential scanning calorimeter (DSC), for example the calorimeter sold under the name DSC 30 by Mettler. The waxes can be hydrocarbon, fluorinated and/or silicone waxes and can be of vegetable, mineral, animal and/or synthetic origin. In particular, the waxes exhibit a melting point of greater than 30° C. and better still of greater than 45° C. Mention may be made, as wax which can be used in the composition of the invention, of beeswax, carnauba or candelilla wax, paraffin wax, microcrystalline waxes, ceresin or ozokerite; synthetic waxes, such as polyethylene or Fischer-Tropsch waxes; or silicone waxes, such as alkyl or alkoxy dimethicones having from 16 to 45 carbon atoms.

The gums are generally polydimethylsiloxanes (PDMSs) of high molecular weight or cellulose gums or polysaccharides and the pasty substances are generally hydrocarbon compounds, such as lanolins and their derivatives, or also PDMSs.

The term "pasty fatty substance" is understood to mean a viscous product comprising a liquid fraction and a solid fraction. It is intended in particular to mean fatty substances having a melting point ranging from 20 to 55° C. and/or a viscosity at 40° C. ranging from 0.1 to 40 Pa·s (1 to 400 poises), measured with a Contraves TV or Rheomat 80. A person skilled in the art can choose, from the MS-r3 and MS-r4 spindles, on the basis of their general knowledge, the spindle which makes it possible to measure the viscosity, so as to be able to carry out the measurement of the viscosity of the pasty compound tested. Preferably, these fatty substances are hydrocarbon compounds (mainly comprising carbon and hydrogen atoms and optionally ester groups), optionally of polymer type; they can also be chosen from silicone compounds and/or fluorinated compounds; they can also be provided in the form of a mixture of hydrocarbon compounds and/or silicone compounds and/or fluorinated compounds. In the case of a mixture of different pasty fatty substances, use is predominantly made, preferably, of pasty hydrocarbon compounds. Mention may be made, among the pasty compounds capable of being used in the composition according to the invention, of lanolins and lanolin derivatives, such as acetylated lanolins or oxypropylenated lanolins or isopropyl lanolate; esters of fatty acids or fatty alcohols, in particular those having from 20 to 65 carbon atoms, such as triisostearyl citrate or cetyl citrate; arachidyl propionate; polyvinyllaurate; cholesterol esters, such as triglycerides of vegetable origin, for example hydrogenated vegetable oils, viscous polyesters, such as poly(12-hydroxystearic acid), and their mixtures. Use may be made, as triglycerides of vegetable origin, of hydrogenated castor oil derivatives. Mention may also be made of silicone pasty fatty substances, such as polydimethylsiloxanes (PDMSs) having pendant chains of the alkyl or alkoxy type having from 8 to 24 carbon atoms, such as stearyl dimethicones.

The nature and the amount of the solid substances depend on the mechanical properties and on the textures desired. By way of indication, the composition can comprise from 0.1 to 50% by weight of waxes, in particular from 1 to 30% by weight of waxes, with respect to the total weight of the composition; it is also possible for it not to comprise waxes or solid fatty substances (0%).

The composition can also comprise a hydrophilic medium comprising water and/or one or more hydrophilic organic solvents, such as linear or branched $C_2$-$C_5$ alcohols and in particular monoalcohols, such as ethanol, isopropanol or n-propanol; polyols, such as glycerol, diglycerol, propylene glycol, sorbitol or pentylene glycol; polyethylene glycols, or alternatively $C_2$ ethers and hydrophilic $C_2$-$C_4$ aldehydes. The water and/or the hydrophilic organic solvents can be present in the composition according to the invention in a content of from 1 to 80% by weight, with respect to the total weight of the composition. The composition can also be anhydrous (0% water).

The composition according to the invention can also comprise one or more colouring materials chosen from pulverulent compounds, such as pigments, fillers, pearlescent agents and glitter, and/or fat-soluble or water-soluble dyes.

The colouring materials, in particular pulverulent colouring materials, can be present in the composition in a content of from 0.01 to 50% by weight, with respect to the weight of the composition, preferably from 0.1 to 40% by weight, indeed even from 1 to 30% by weight.

The term "pigments" should be understood as meaning white or coloured and inorganic or organic particles of any shape which are insoluble in the physiological medium and which are intended to colour the composition.

The term "pearlescent agents" should be understood as meaning iridescent particles of any shape produced in particular by certain shellfish in their shells or else synthesized.

The pigments can be white or coloured, inorganic and/or organic and interferential or noninterferential. Mention may be made, among inorganic pigments, of titanium dioxide, optionally surface-treated, zirconium or cerium oxides, and also iron or chromium oxides, manganese violet, ultramarine blue, chromium hydrate and ferric blue. Mention may be made, among organic pigments, of carbon black, pigments of D & C type, and lakes, based on cochineal carmine, of barium, strontium, calcium or aluminium.

The pearlescent pigments can be chosen from white pearlescent pigments, such as mica covered with titanium oxide or with bismuth oxychloride, coloured pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride.

The term "fillers" should be understood as meaning colourless or white, inorganic or synthetic and lamellar or nonlamellar particles intended to give body or stiffness to the composition and/or softness, mattness and uniformity to the makeup. The fillers can be inorganic or organic and of any shape, platelet, spherical or oblong. Mention may be made of talc, mica, silica, kaolin, Nylon, poly-β-alanine and polyethylene powders, Teflon, lauroyl lysine, starch, boron nitride, tetrafluoroethylene polymer powders, hollow microspheres, such as Expancel (Nobel Industrie), Polytrap (Dow Corning) and silicone resin microbeads (Tospearls from Toshiba, for example), precipitated calcium carbonate, magnesium carbonate and basic magnesium carbonate, hydroxyapatite, hollow silica microspheres (Silica Beads from Maprecos), glass or ceramic microcapsules, or metal soaps derived from organic carboxylic acids having from 8 to 22 carbon atoms, preferably from 12 to 18 carbon atoms, for example zinc stearate, magnesium stearate, lithium stearate, zinc laurate or magnesium myristate.

The fat-soluble dyes are, for example, Sudan red, DC Red 17, DC Green 6, β-carotene, soybean oil, Sudan brown, DC Yellow 11, DC Violet 2, DC Orange 5 or quinoline yellow. They can represent from 0.01 to 20% of the weight of the composition and better still from 0.1 to 6%.

The water-soluble dyes are, for example, beetroot juice or methylene blue and can represent from 0.01 to 6% of the total weight of the composition.

The composition according to the invention can also comprise ingredients commonly used in cosmetics, such as vitamins, thickeners, gelling agents, trace elements, softeners, sequestering agents, fragrances, basifying or acidifying agents, preservatives, sunscreens, surfactants, antioxidants, cosmetic active principles, propellants, ceramides, additional agents which are able to form a film, polymers, in particular film-forming polymers, or their mixtures. Of course, a person skilled in the art will take care to choose this or these optional additional ingredients and/or their amount so that the advantageous properties of the composition according to the invention are not, or not substantially, detrimentally affected by the envisaged addition.

The composition according to the invention can be provided in the form of a suspension or a dispersion, in particular of oil in water, by virtue of vesicles; an optionally thickened, indeed even gelled, aqueous or oily solution; an oil-in-water, water-in-oil or multiple emulsion; a gel or a foam; an oily or emulsified gel; a dispersion of vesicles, in particular of lipid vesicles; a two-phase or multiphase lotion; a spray; a loose, compact or cast powder; or an anhydrous paste. This composition can have the appearance of a lotion, of a cream, of a salve, of a soft paste, of an ointment, of a foam, of a cast or moulded solid, in particular in the form of a stick or in a dish, or of a compacted solid.

A person skilled in the art can choose the appropriate formulation form and its method of preparation on the basis of his general knowledge, taking into account, on the one hand, the nature of the constituents used, in particular their solubility in the support, and, on the other hand, the application envisaged for the composition.

The cosmetic composition according to the invention can be provided in the form of a care and/or make-up product for the skin of the body or of the face, the lips, the nails, the eyelashes, the eyebrows and/or the hair, of an antisun or self-tanning product, or of a hair product for caring for, treating, cleaning, conditioning, shaping, making up or dyeing the hair.

It can thus be provided in the form of a makeup composition, in particular a product for the complexion, such as a foundation, a face powder or an eye shadow; a product for the lips, such as a lipstick, a gloss or a lip care product; a concealer; a blusher, a mascara or an eyeliner; a product for making up the eyebrows, a lip pencil or an eye pencil; a product for the nails, such as a nail varnish or a nail care product; a product for making up the body; or a product for making up the hair (hair mascara).

It can also be provided in the form of a protecting, cleaning, hygiene or care composition for the skin of the face, of the neck, of the hands or of the body, in particular an antiwrinkle composition; a moisturizing or treating composition; an antisun or artificial tanning (self-tanning) composition; or a deodorant or antiperspirant composition.

It can also be provided in the form of a hair product, in particular for the dyeing, the form retention of the hairstyle or the shaping of the hair or the care, the treatment or the cleaning of the hair, such as shampoos, gels, hairsetting lotions, blow drying lotions or fixing and styling compositions, such as lacquers or sprays.

Preferably, the cosmetic composition according to the invention is provided in the form of a product for making up the body, lips, eyelashes, hair or nails, optionally having nontherapeutic treatment and/or care properties.

It is provided very particularly in the form of a lipstick or of a lip gloss, of a lip balm, of a face powder, of an eye shadow, of a foundation, of a body painting product, of a mascara, of an eyeliner, of a nail varnish, of an antiperspirant, of a product for the artificial tanning of the skin or of a product for dyeing or caring for the hair.

Another subject-matter of the invention is a method for the cosmetic treatment of keratinous substances, such as the skin of the body or of the face, lips, nails, hair, eyebrows and/or eyelashes, comprising the application, to the said substances, of a cosmetic composition as defined above.

Preferably, it is a method for making up the skin, lips, eyelashes, nails, eyebrows and/or hair.

The invention is illustrated in more detail in the following examples.

EXAMPLE 1

Synthesis of the n-$C_{18}$ Monoester of Formula (I) with Y=n-$C_{17}$; R'=H; R1, R2, R3, R4, R5, R'1, R'2, R'3, R'4, R'5=H

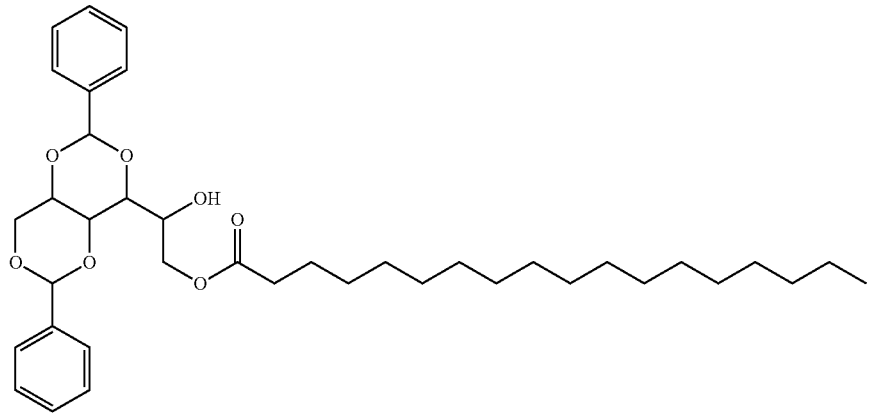

38.0 g (37.6 mmol) of triethylamine are added to a suspension of 90.0 g (25.1 mmol) of dibenzylidene sorbitol in 1600 ml of acetonitrile and the mixture is heated at reflux until dissolution is complete. 83.3 g of stearoyl chloride (27.5 mmol) are then added and the mixture is maintained at reflux for 6 hours.

After cooling the reaction medium, the formation of a precipitate is observed. The precipitate is filtered off on a sintered glass filter and then copiously washed with water. After drying at 40° C. under reduced pressure, 142 g of the expected compound are obtained in the form of a white solid with the melting point: 119-122° C.

The $^1H$ and $^{13}C$ ($d_6$-pyridine) NMR spectra are in accordance with the expected structure.

EXAMPLE 2

Synthesis of the Iso-$C_{18}$ Monoester of Formula (I) with Y=Iso-$C_{17}$; R'=H; R1, R2, R3, R4, R5, R'1, R'2, R'3, R'4, R'5=H

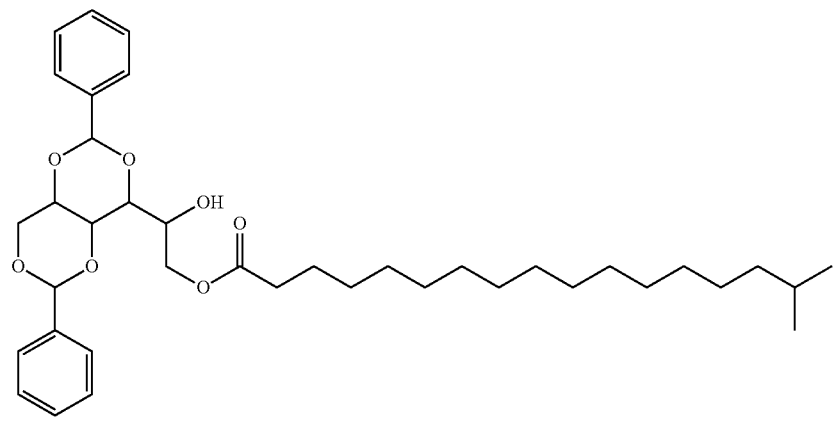

5.65 g (55.8 mmol) of triethylamine are added to a suspension of 10 g (27.9 mmol) of dibenzylidene sorbitol in 350 ml of acetonitrile; the mixture is heated at reflux until dissolution is complete. 8.45 g of isostearoyl chloride (27.9 mmol) are then added and the mixture is maintained at reflux for 6 hours. After cooling the reaction medium, it is poured into a large volume of ice-cold water. The precipitate obtained is filtered off on a sintered glass filter and then copiously washed with water. After drying at 40° C. under reduced pressure, 12.09 g of the expected compound are obtained in the form of a beige solid with the melting point: 124° C. The $^1$H and $^{13}$C ($d_6$-pyridine) NMR spectra are in accordance with the expected structure.

EXAMPLE 3

Synthesis of the Iso-$C_{16}$ Monoester of Formula (I) with Y=Iso-$C_{15}$; R'=H; R1, R2, R3, R4, R5, R'1, R'2, R'3, R'4, R'5=H

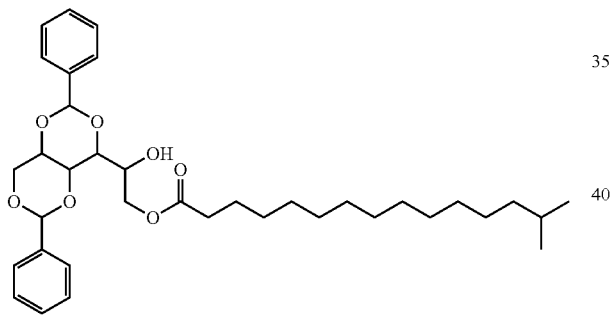

A suspension of 5.0 g (13.95 mmol) of dibenzylidene sorbitol in 175 ml of acetonitrile is heated at reflux until dissolution is complete, 2.82 g (27.9 mmol) of triethylamine and 3.8 g (13.95 mmol) of isohexadecanoyl chloride are then added and the mixture is maintained at reflux for 5 hours. After cooling the reaction medium, it is poured into a large volume of ice-cold water. The precipitate obtained is filtered off on a sintered glass filter and then copiously washed with water. After drying at 40° C. under reduced pressure, 6.39 g of the expected compound are obtained in the form of a beige solid with the melting point: 162° C.

The $^1$H and $^{13}$C ($d_6$-pyridine) NMR spectra are in accordance with the expected structure.

EXAMPLE 4

Synthesis of the Diester Iso-$C_{16}$/n-$C_{18}$ of Formula (I) with Y=Iso-$C_{15}$, Y'=n-$C_{17}$; R1, R2, R3, R4, R5, R'1, R'2, R'3, R'4, R'5=H

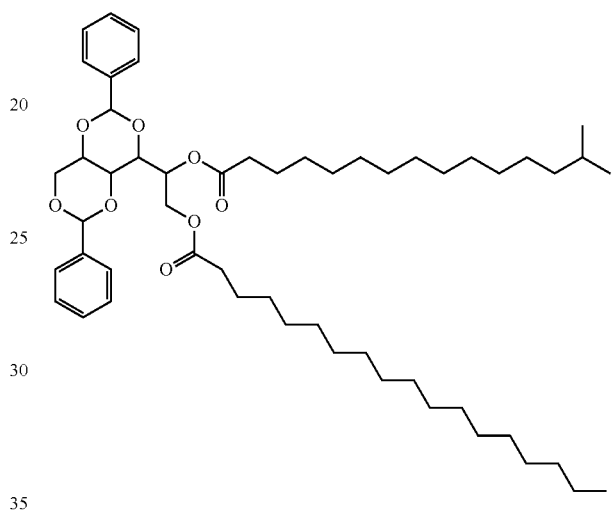

8.35 g (82.26 mmol) of triethylamine are added to a suspension of 13.4 g (37.3 mmol) of dibenzylidene sorbitol in 300 ml of acetonitrile and the mixture is heated at reflux until dissolution is complete. 11.38 g of stearoyl chloride (37.3 mmol) are then added and the mixture is maintained at reflux for 4 hours. 8.3 g (82.02 mmol) of triethylamine are again added, followed by 10.31 g (37.5 mmol) of isohexadecanoyl chloride, and the mixture is maintained at reflux overnight. After cooling the reaction medium, the formation of a white precipitate is observed. The precipitate is filtered off on a sintered glass filter and then washed with water and with ethanol. After drying at 40° C. under reduced pressure, 21.18 g of the crude diester are obtained, which product is purified by chromatography on silica gel in the methyl ethyl ketone:cyclohexane 1:1 eluent mixture. 16.8 g of the expected compound are obtained in the form of a white solid with the melting point: 82.9° C.

The $^1$H and $^{13}$C ($d_6$-pyridine) NMR spectra are in accordance with the expected structure.

EXAMPLE 5

Synthesis of the Sebacic Ester of Formula (II) with A=C$_8$H$_{16}$; R''=H; R1, R2, R3, R4, R5, R'1, R'2, R'3, R'4, R'5=H

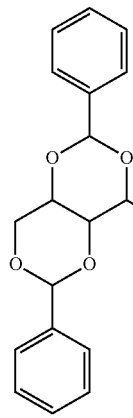
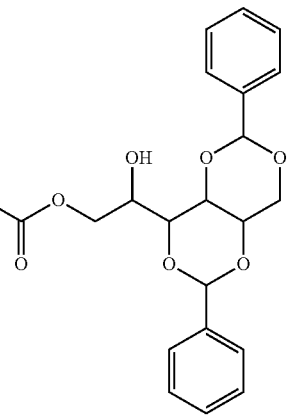

A suspension of 10 g (27.9 mmol) of dibenzylidene sorbitol in 300 ml of acetonitrile is heated at reflux until dissolution is complete, 3.106 g (30.69 mmol) of triethylamine and 3.336 g (13.95 mmol) of sebacoyl chloride are then added and the mixture is maintained at reflux for 10 hours. After cooling the reaction medium, it is poured into a large volume of ice-cold water. The precipitate obtained is filtered off on a sintered glass filter and then copiously washed with water. After drying at 40° C. under reduced pressure, 8.28 g of expected compound are obtained in the form of a beige solid with the melting point: 170° C.

The $^1$H and $^{13}$C (d$_6$-pyridine) NMR spectra are in accordance with the expected structure.

EXAMPLE 6

Synthesis of the Silicone Ester of Formula (II) Below (R''=H; R1, R2, R3, R4, R5, R'1, R'2, R'3, R'4, R'5=H)

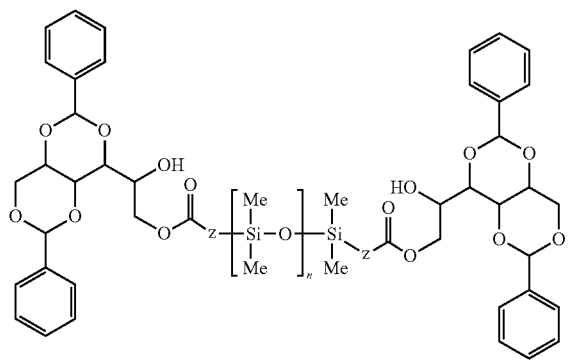

with Z = (CH$_2$)$_3$
and n = 34

A suspension of 1.03 g (2.88 mmol) of dibenzylidene sorbitol and 4.02 g of α,ω-dicarboxy silicone sold under the name Tegomer C—Si 2342 by Goldschmidt in 25 ml of acetonitrile is placed in a microwave oven with a power of 75 watts at 130° C. for 30 minutes. The mixture is allowed to cool and then water is added to the gel obtained. A white precipitate is formed. It is filtered off on a sintered glass filter and then copiously washed with water. After drying at 40° C. under reduced pressure, 3.16 g of the expected compound are obtained in the form of a beige solid with the melting point: 191° C.

The $^1$H and $^{13}$C (d$_6$-pyridine) NMR spectra are in accordance with the expected structure.

EXAMPLE 7

Synthesis of the n-C$_{10}$ Monoester of Formula (I) with Y=n-C$_9$; R'=H; R1, R2, R3, R4, R5, R'1, R'2, R'3, R'4, R'5=H

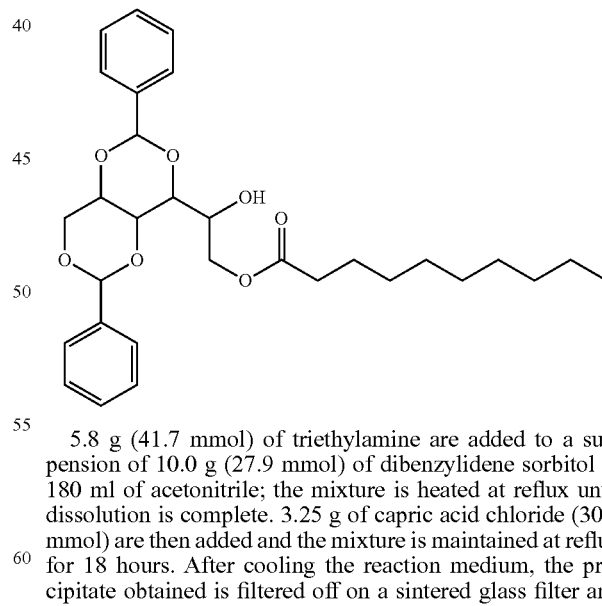

5.8 g (41.7 mmol) of triethylamine are added to a suspension of 10.0 g (27.9 mmol) of dibenzylidene sorbitol in 180 ml of acetonitrile; the mixture is heated at reflux until dissolution is complete. 3.25 g of capric acid chloride (30.6 mmol) are then added and the mixture is maintained at reflux for 18 hours. After cooling the reaction medium, the precipitate obtained is filtered off on a sintered glass filter and then washed with water. After drying at 40° C. under reduced pressure, 6 g of the expected compound are obtained in the form of a white solid with the melting point: 123° C.

The $^1$H and $^{13}$C (d$_6$-DMSO) NMR spectra are in accordance with the expected structure.

EXAMPLE 8

Synthesis of the n-$C_{18}$/n-$C_{18}$ Diester of Formula (I) with Y=Y'=n-$C_{17}$; R1, R2, R3, R4, R5, R'1, R'2, R'3, R'4, R'5=H

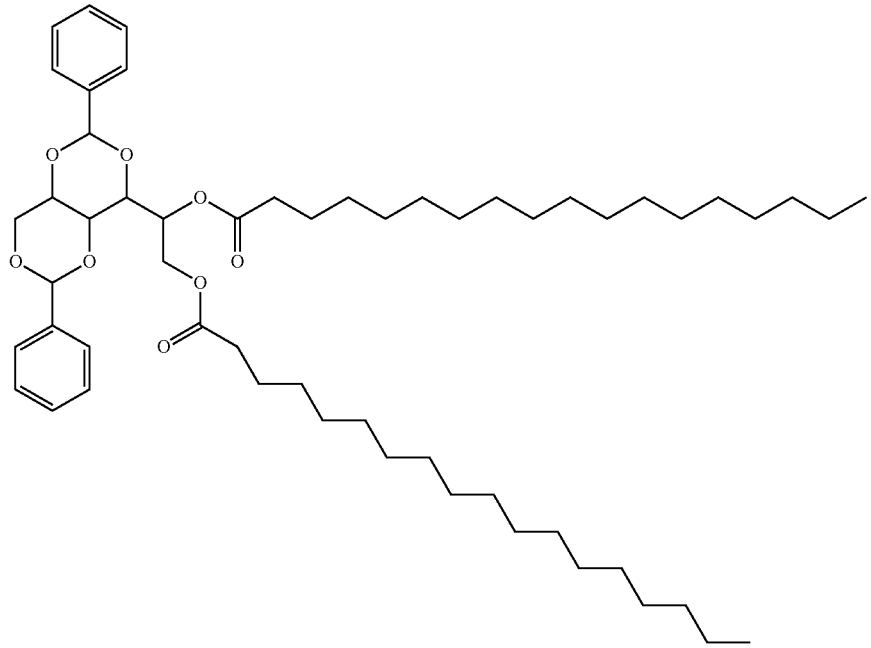

37.2 g (368 mmol) of triethylamine are added to a suspension of 30.0 g (83.7 mmol) of dibenzylidene sorbitol in 1000 ml of acetonitrile; the mixture is heated at reflux until dissolution is complete. 55.8 g of stearic acid chloride (184 mmol) are then added and the mixture is maintained at reflux for 18 hours. After cooling the reaction medium, it is poured into 1 liter of ice-cold water. The precipitate obtained is filtered off on a sintered glass filter and then washed with 500 ml of ethanol. After drying at 40° C. under reduced pressure, 73.6 g of the expected compound are obtained in the form of a white solid with the melting point: 103° C.

The $^1H$ and $^{13}C$ ($d_6$-pyridine) NMR spectra are in accordance with the expected structure.

EXAMPLE 9

Synthesis of the Ester of Formula (II) with A=$C_{34}H_{68}$ Dimer; R"=H; R1, R2, R3, R4, R5, R'1, R'2, R'3, R'4, R'5=H

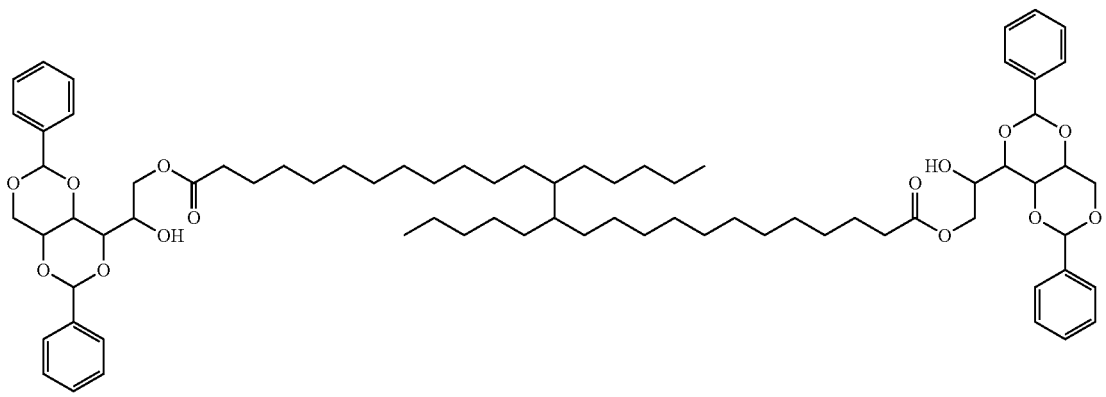

18.7 g (180 mmol) of triethylamine are added to a suspension of 47.6 g (130 mmol) of dibenzylidene sorbitol in 1000 ml of acetonitrile; the mixture is heated at reflux until dissolution is complete. 40.0 g of Pripol 1009 chloride (66 mmol) are then added and the mixture is maintained at reflux for 17 hours. After cooling the reaction medium, it is poured into 1 liter of ice-cold water. The precipitate obtained is filtered off on a sintered glass filter and then washed with 500 ml of ethanol. After drying at 40° C. under reduced pressure, 54.4 g of the expected compound are obtained in the form of a beige solid with the melting point: 178° C.

The $^1$H and $^{13}$C ($d_6$-pyridine) NMR spectra are in accordance with the expected structure.

EXAMPLE 10

Synthesis of the n-$C_{16}$ Monoester of Formula (I) with Y=n-$C_{15}$ R'=H; R1, R2, R3, R4, R5, R'1, R'2, R'3, R'4, R'5=H

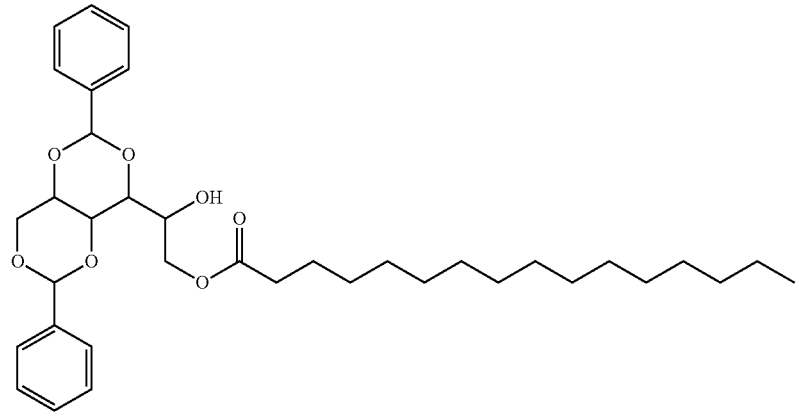

12.2 g (120.6 mmol) of triethylamine are added to a suspension of 18.0 g (50.3 mmol) of dibenzylidene sorbitol in 400 ml of acetonitrile; the mixture is heated at reflux until dissolution is complete. 15.2 g of palmitic acid chloride (55.3 mmol) are added and the mixture is maintained at reflux for 22 hours. After cooling the reaction medium, it is poured into a large volume of ice-cold water. The precipitate obtained is filtered off on a sintered glass filter and then copiously washed with water. After drying at 40° C. under reduced pressure, 28 g of the expected compound are obtained in the form of a white solid with the melting point: 115° C.

The $^1$H and $^{13}$C ($d_6$-pyridine) NMR spectra are in accordance with the expected structure.

EXAMPLE 11

Synthesis of the n-$C_{18}$ Monoester of Formula (I) with Y=n-$C_{17}$; R'=H; R1, R2, R4, R5, R'1, R'2, R'4, R'5=H; R3=R'3=propyl

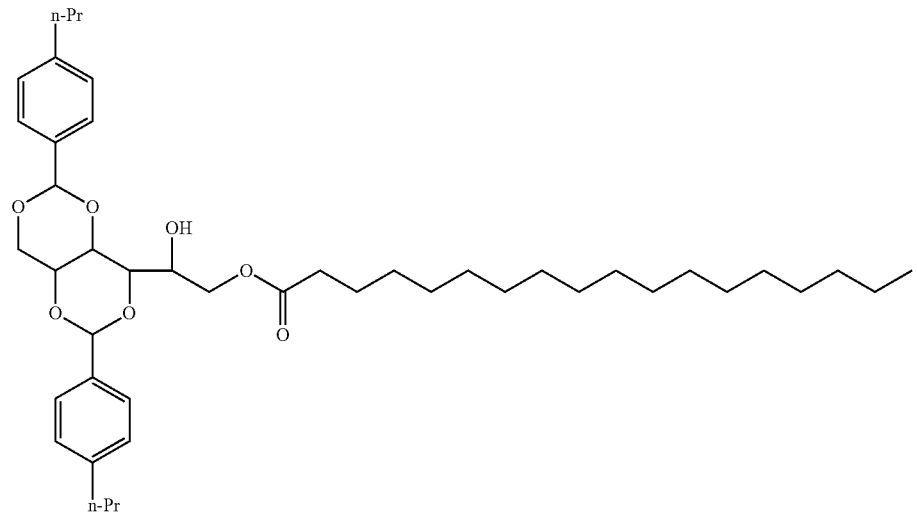

10.9 g (84.5 mmol) of diisopropylethylamine are added to a suspension of 25.0 g (56.5 mmol) of n-propyldibenzylidene sorbitol in 200 ml of acetonitrile; the mixture is heated at reflux until dissolution is complete. 18.8 g of stearic acid chloride (63.1 mmol) are added and the mixture is maintained at reflux for 18 hours. After cooling the reaction medium, it is poured into 1 liter of ice-cold water. The precipitate obtained is filtered off on a sintered glass filter and then washed with 500 ml of ethanol. After drying at 40° C. under reduced pressure, 19.3 g of the expected compound are obtained in the form of a beige solid with the melting point: 51° C.

EXAMPLE 12

Synthesis of the n-$C_{18}$ Monoester of Formula (I) with Y=n-$C_{17}$; R'=H; R1, R2, R4, R5, R'1, R'2, R'4, R'5=H; R3=R'3=Isopropyl

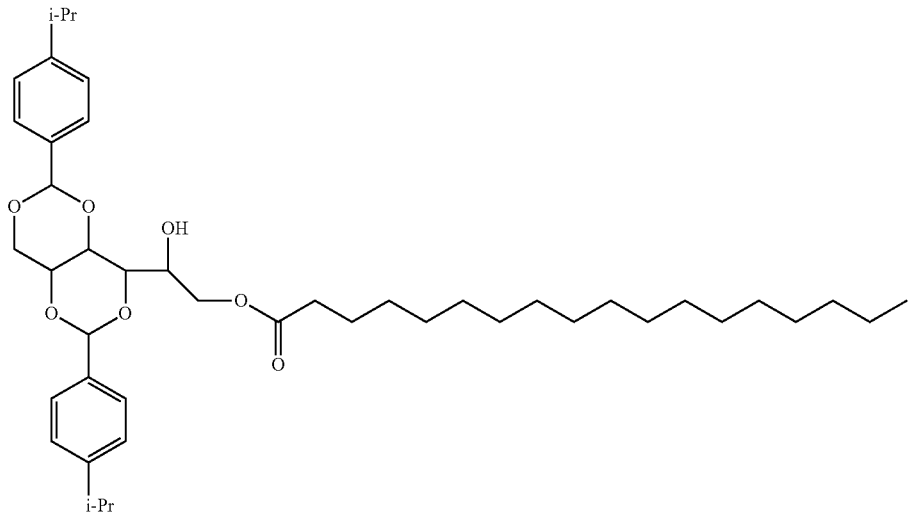 [SMILES: CCCCCCCCCCCCCCCCCC(=O)OCC(O)C1OC(c2ccc(C(C)C)cc2)OC2COC(c3ccc(C(C)C)cc3)OC21]

10.9 g (84.5 mmol) of diisopropylethylamine are added to a suspension of 25.0 g (56.5 mmol) of isopropyldibenzylidene sorbitol in 200 ml of acetonitrile; the mixture is heated at reflux until dissolution is complete. 18.8 g of stearic acid chloride (63.1 mmol) are added and the mixture is maintained at reflux for 18 hours. After cooling the reaction medium, it is poured into 1 liter of ice-cold water. The precipitate obtained is filtered off on a sintered glass filter and then washed with 500 ml of ethanol. After drying at 40° C. under reduced pressure, 32.3 g of the expected compound are obtained in the form of a beige solid with the melting point: 126° C.

EXAMPLE 13

Synthesis of the n-$C_{18}$ Monoester of Formula I with Y=n-$C_{17}$; R'=H; R1, R2, R4, R5, R'1, R'2, R'4, R'5=H; R3=R'3=isobutyle

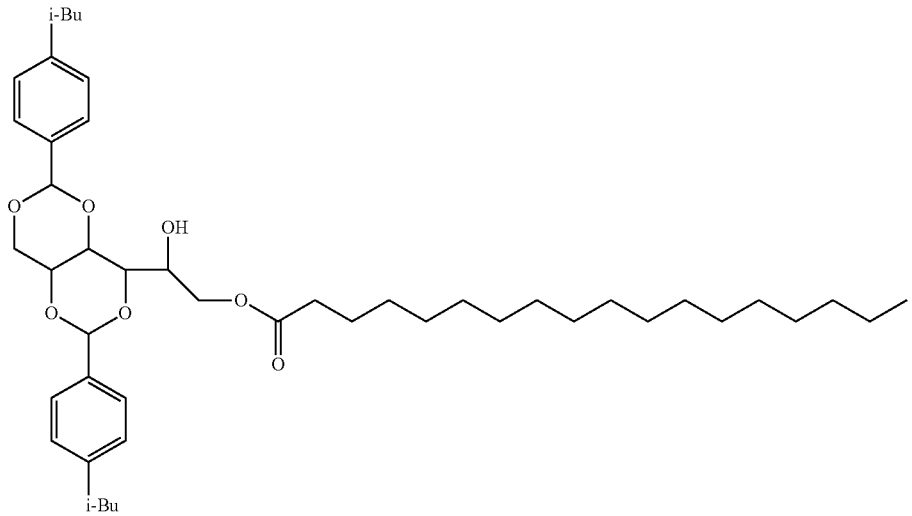

10.3 g (79.7 mmol) of diisopropylethylamine are added to a suspension of 25.0 g (53.1 mmol) of isobutyldibenzylidene sorbitol in 200 ml of acetonitrile; the mixture is heated at reflux until dissolution is complete. 17.7 g of stearic acid chloride (58.4 mmol) are then added and the mixture is maintained at reflux for 18 hours. After cooling the reaction medium, it is poured into 1 liter of ice-cold water. The precipitate obtained is filtered off on a sintered glass filter and then washed with 500 ml of ethanol. After drying at 40° C. under reduced pressure, 8.7 g of the expected compound are obtained in the form of a beige solid with the melting point: 117° C.

EXAMPLE 14

Synthesis of the n-$C_{18}$/n-$C_{18}$ Diester of Formula I with Y=Y'=n-$C_{17}$; R1, R2, R4, R5, R'1, R'2, R'4, R'5=H; R3=R'3=propyl

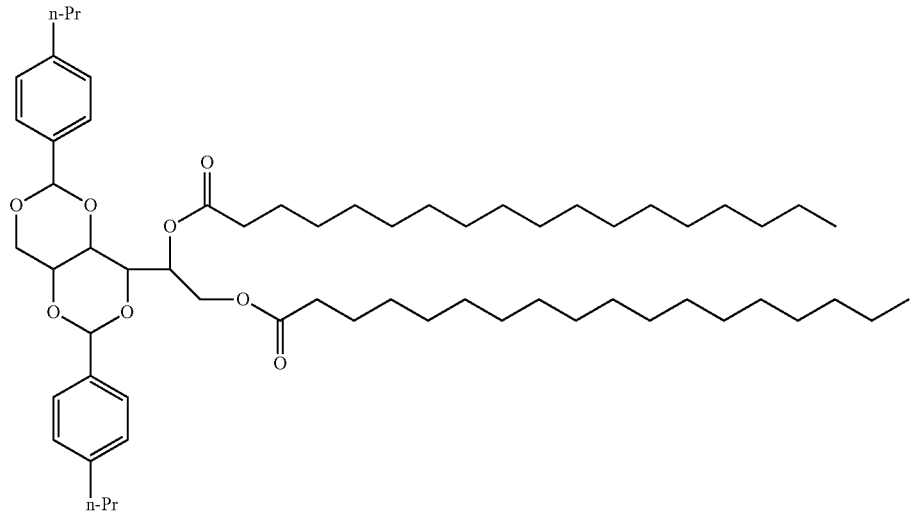

14.6 g (113 mmol) of diisopropylethylamine are added to a suspension of 20.0 g (45.2 mmol) of n-propyldibenzylidene sorbitol in 300 ml of acetonitrile; the mixture is heated at reflux until dissolution is complete. 28.8 g of stearic acid chloride (94.9 mmol) are added and the mixture is maintained at reflux for 18 hours. After cooling the reaction medium, it is poured into 1 liter of ice-cold water. The precipitate obtained is filtered off on a sintered glass filter and then washed with 500 ml of ethanol. After drying at 40° C. under reduced pressure, 24.3 g of the expected compound are obtained in the form of a beige solid with the melting point: 70° C.

EXAMPLE 15

Synthesis of the n-$C_{18}$ monoester of formula I with Y=n-$C_{17}$; R2, R3, R'2, R'3=$CH_3$; R'=H; R1, R4, R5, R'1, R'4, R'5=H

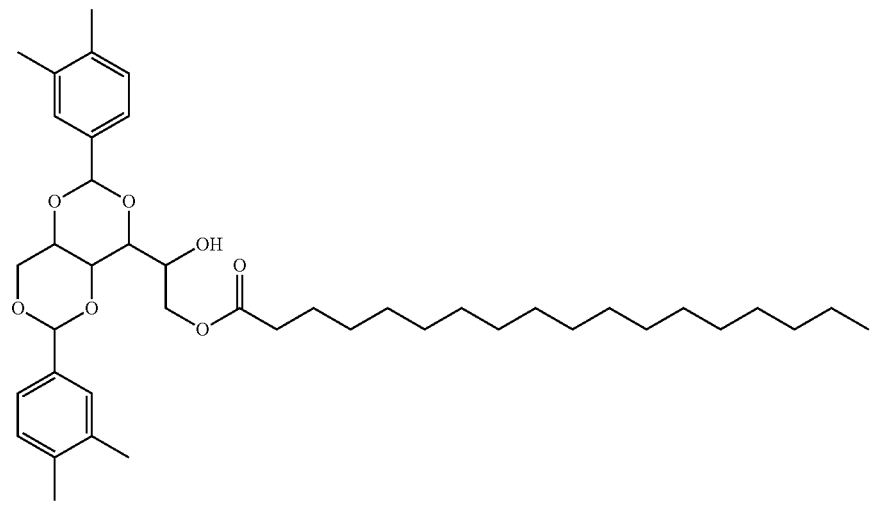 [SMILES: CCCCCCCCCCCCCCCCCC(=O)OCC(O)C1OC(c2ccc(C)c(C)c2)OC2COC(c3ccc(C)c(C)c3)OC21]

9.4 g (72.4 mmol) of diisopropylethylamine are added to a suspension of 20 g (48.3 mmol) of 3,4-dimethylbenzylidene sorbitol in 400 ml of acetonitrile, and the mixture is heated at reflux for 1 hour; the product remains dispersed. 16.1 g of stearoyl chloride (53.1 mmol) are added and the mixture is maintained at reflux for 24 hours. After cooling the reaction medium, the formation of a precipitate is observed. The precipitate is filtered off on a sintered glass filter and then copiously washed with water (4×250 ml) and then with absolute ethanol (4×250 ml). After drying at 60° C. under reduced pressure, 23.4 g of the expected compound are obtained in the form of a white solid with a melting point: 108° C. The $^1H$ and $^{13}C$ ($d_6$-pyridine) NMR spectra are in accordance with the expected structure.

EXAMPLE 16

The following 3 lipstick sticks were prepared:

Stick No. 1

| | | |
|---|---|---|
| Compound of Example 1 | 12.5% | |
| DC Red 7 | 5% | |
| Parleam | q.s. for 100% | |

Stick No. 2

| | | |
|---|---|---|
| Compound of Example 1 | 12.5% | |
| Iron oxides | 5% | |
| Parleam | q.s. for 100% | |

Stick n° 3

| | | |
|---|---|---|
| Compound of Example 1 | 12.5% | |
| Pearlescent agent-glitter | 5% | |
| Parleam | q.s. for 100% | |

It is found that the three sticks are glossy and disintegrate very readily.

The invention claimed is:

1. A compound of dibenzylidene sorbitol ester type of formula (I):

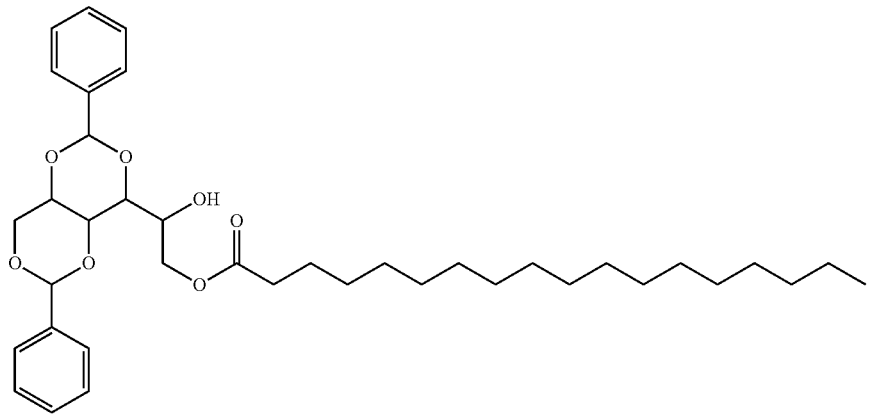

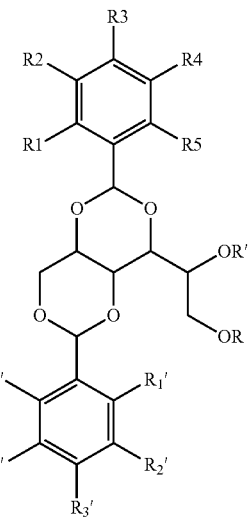

(I)

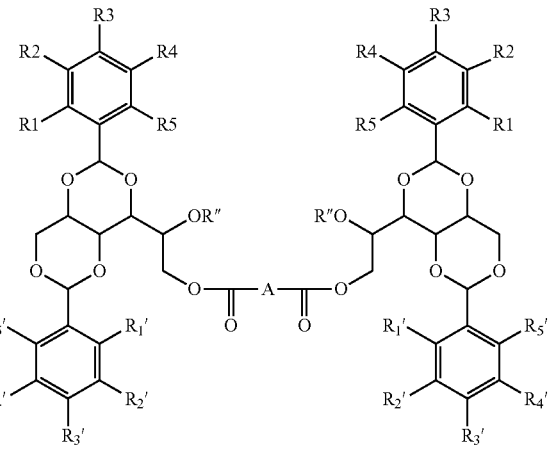

(II)

in which:
R and R', independently of one another, a hydrogen atom or a —C(O)Y radical in which Y represents:
a saturated or unsaturated linear or branched $C_2$-$C_{25}$ hydrocarbon radical;
the R1, R2, R3, R4, R5, R'1, R'2, R'3, R'4 and R'5 radicals each represent a hydrogen atom.

2. A compound selected from the group consisting of the following compounds:

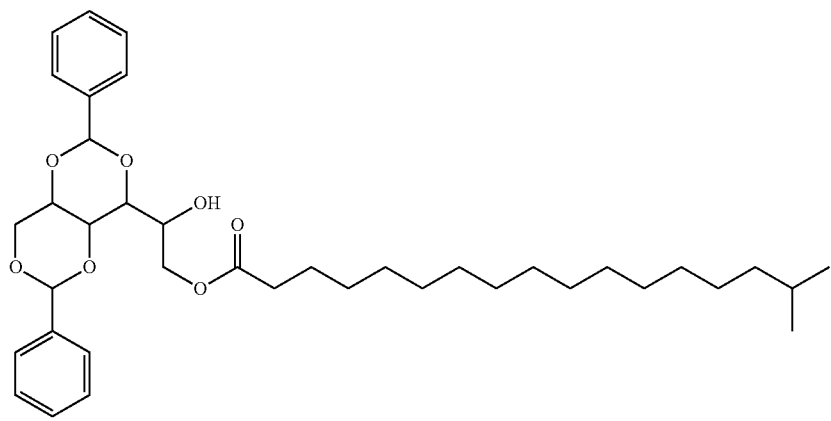
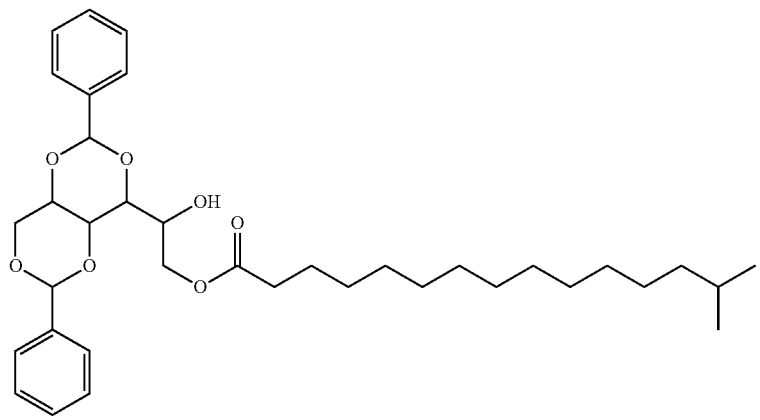
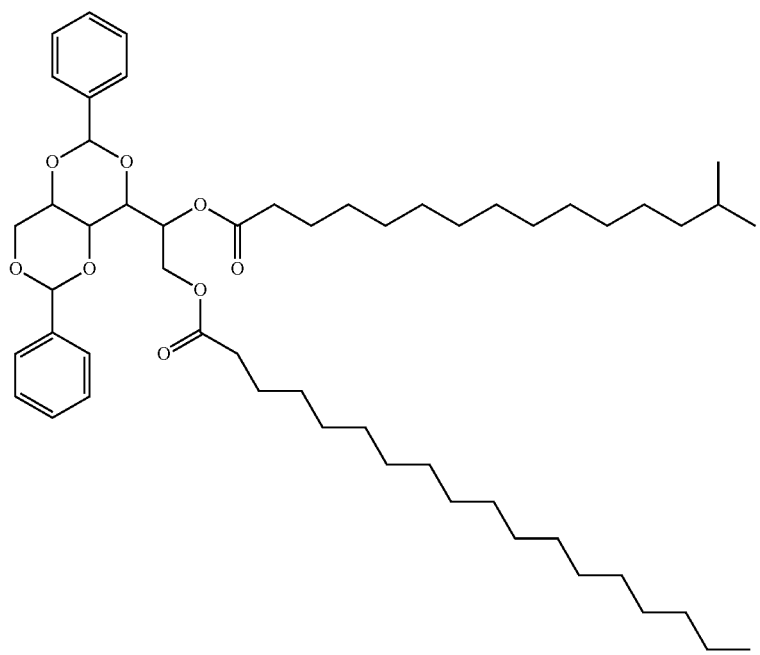

-continued
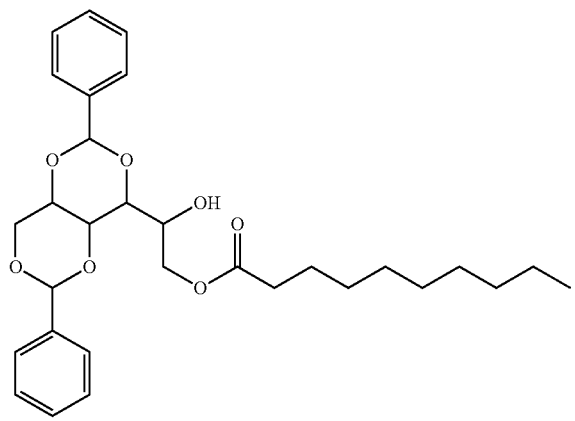
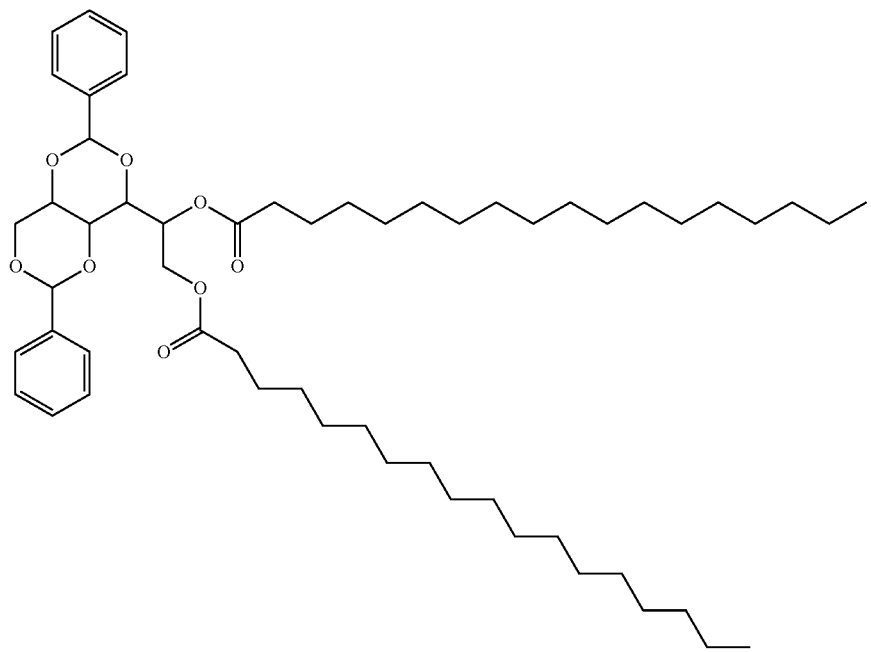 [SMILES: CCCCCCCCCCCCCCCCCC(=O)OCC(OC(=O)CCCCCCCCCCCCCCCCC)C1OC(c2ccccc2)OC2COC(c3ccccc3)OC21]
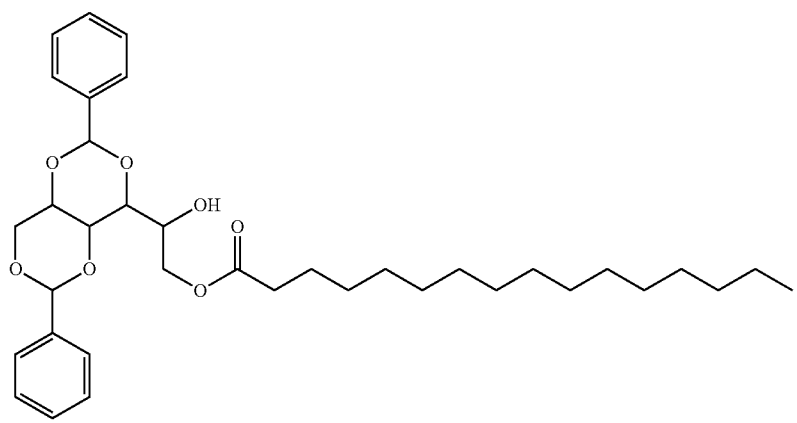

-continued

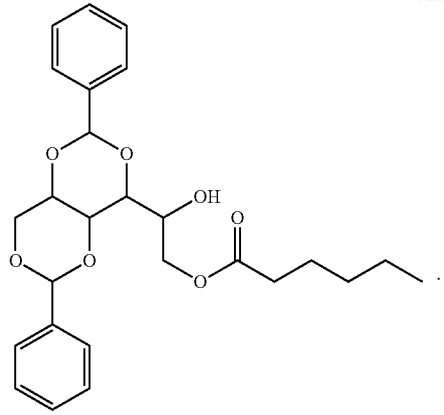

3. Process for the preparation of the compounds of formula (I) as defined claim 1, comprising a stage in which a dibenzylidene sorbitol derivative of formula (A) below is reacted with at least one acid halide of formula Y—C(O)-Hal in an aprotic solvent in the presence of a base:

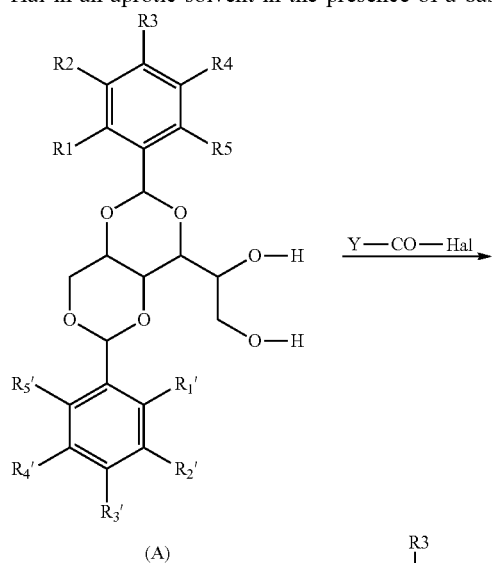

4. A cosmetic or pharmaceutical composition comprising, in a physiologically acceptable medium, at least one compound of formula (I) as defined in claim 1.

5. The composition according to claim 4, in which the compound of formula (I), alone or as a mixture, is present in an amount of between 0.05 and 30% by weight with respect to the total weight of the final cosmetic or pharmaceutical composition.

6. The composition according to claim 4, comprising at least one ingredient chosen from volatile or nonvolatile and carbon-comprising, hydrocarbon-comprising, fluorine-comprising and/or silicone-comprising oils and/or solvents of mineral, animal, vegetable or synthetic origin.

7. The composition according to claim 4, which is provided in the form of a care, hygiene or makeup product for the skin of the body or of the face, the lips, the nails, the eyelashes or the eyebrows; of an antisun or self-tanning product; or of a hair product.

8. Method for the cosmetic treatment of keratinous substances comprising the application, to the said substances, of a cosmetic composition as defined in claim 4.

9. The compound according to claim 1, being represented by the following structure:

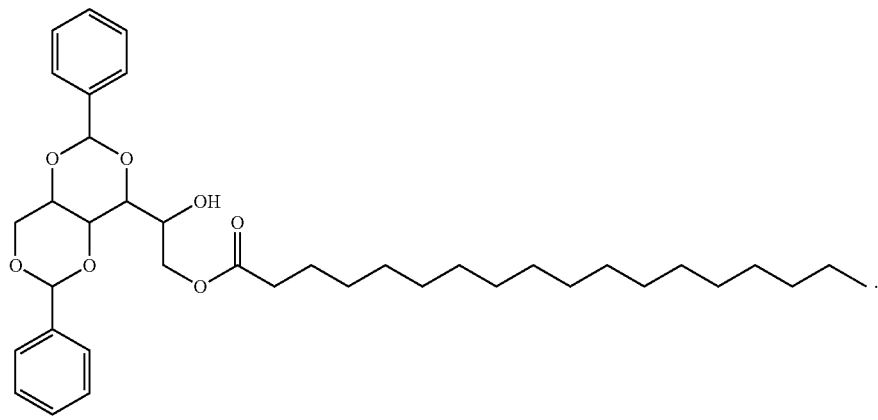 [SMILES: CCCCCCCCCCCCCCCCCC(=O)OCC(O)C1OC(c2ccccc2)OC2COC(c3ccccc3)OC21]

10. The compound according to claim 1, wherein in formula (I) R' is hydrogen atom; R is a —C(O)Y radical in which Y represents a saturated and linear or branched $C_2$-$C_{25}$ hydrocarbon radical.

11. The composition according to claim 4, comprising at least one ingredient chosen from waxes, pasty fatty substances or gums of animal, vegetable, mineral or synthetic origin; water; linear or branched $C_2$-$C_5$ alcohols; polyols; polyethylene glycols; $C_2$ ethers; hydrophilic $C_2$-$C_4$ aldehydes; colouring materials; vitamins; thickeners; gelling agents; trace elements; softeners; sequestering agents; fragrances; basifying or acidifying agents; preservatives; sunscreens; surfactants; antioxidants; cosmetic active principles; propellants; ceramides; and auxiliary film forming agents.

12. The composition according to claim 11 wherein the film forming auxiliary film forming agents are film forming polymers.

13. The composition according to claim 4, wherein the $C_2$-$C_5$ alcohols are monoalcohols.

* * * * *